(12) United States Patent
Repasky et al.

(10) Patent No.: US 12,264,069 B2
(45) Date of Patent: Apr. 1, 2025

(54) PROCESS FOR THE CONVERSION OF CARBON DIOXIDE

(71) Applicant: Oxy Low Carbon Ventures, LLC, Houston, TX (US)

(72) Inventors: John M. Repasky, New Braunfels, TX (US); Robert L. Zeller, III, Seabrook, TX (US)

(73) Assignee: Oxy Low Carbon Venture, LLC, Houston, TX (US)

( * ) Notice: Subject to any disclaimer, the term of this patent is extended or adjusted under 35 U.S.C. 154(b) by 213 days.

(21) Appl. No.: 17/763,703

(22) PCT Filed: Sep. 28, 2020

(86) PCT No.: PCT/US2020/053118
§ 371 (c)(1),
(2) Date: Mar. 25, 2022

(87) PCT Pub. No.: WO2021/062384
PCT Pub. Date: Apr. 1, 2021

(65) Prior Publication Data
US 2022/0348461 A1   Nov. 3, 2022

Related U.S. Application Data

(60) Provisional application No. 62/906,969, filed on Sep. 27, 2019.

(51) Int. Cl.
*C01B 3/58* (2006.01)
*B01J 19/00* (2006.01)
(Continued)

(52) U.S. Cl.
CPC ............ *C01B 3/58* (2013.01); *B01J 19/0013* (2013.01); *B01J 19/242* (2013.01); *C01B 32/40* (2017.08);
(Continued)

(58) Field of Classification Search
CPC ... C01B 3/58; C01B 32/40; C01B 2203/0475; C01B 2203/062; C01B 2203/061; B01J 19/242; B01J 19/0013; B01J 2219/00157
See application file for complete search history.

(56) References Cited

U.S. PATENT DOCUMENTS

| | | |
|---|---|---|
| 3,723,344 A | 3/1973 | Reynolds |
| 3,919,114 A | 11/1975 | Reynolds |

(Continued)

FOREIGN PATENT DOCUMENTS

| | | |
|---|---|---|
| CN | 101624186 B | 1/2010 |
| JP | H0769615 A | 3/1995 |

(Continued)

OTHER PUBLICATIONS

International Search Report and Written Opinion for related PCT/US2020/053118 dated Dec. 21, 2020 (12 pp).

*Primary Examiner* — Jafar F Parsa
(74) *Attorney, Agent, or Firm* — Kenner Renner; Arthur M. Reginelli

(57) ABSTRACT

A process for the production of syngas, the process comprising (i) reacting at least a portion of carbon dioxide with hydrogen within an initial reactor to produce an initial product stream including carbon monoxide, water, unreacted carbon dioxide, and unreacted hydrogen; and (ii) reacting at least a portion of the unreacted carbon dioxide and unreacted hydrogen within a reactor downstream of the first reactor to thereby produce a product stream including carbon monoxide, water, unreacted carbon dioxide, and unreacted hydrogen.

22 Claims, 11 Drawing Sheets

(51) Int. Cl.
*B01J 19/24* (2006.01)
*C01B 32/40* (2017.01)
*C07C 1/04* (2006.01)
*C07C 29/151* (2006.01)

(52) U.S. Cl.
CPC ........ *C07C 1/0485* (2013.01); *C07C 29/1518* (2013.01); *B01J 2219/00157* (2013.01); *C01B 2203/0435* (2013.01); *C01B 2203/0475* (2013.01); *C01B 2203/061* (2013.01); *C01B 2203/062* (2013.01)

(56) References Cited

U.S. PATENT DOCUMENTS

| | | |
|---|---|---|
| 2003/0113244 A1 | 3/2003 | Dupont |
| 2006/0211777 A1 | 9/2006 | Severinsky |
| 2010/0280135 A1 | 11/2010 | Doty |
| 2011/0054047 A1* | 3/2011 | Severinsky ............... C01B 3/16 422/186 |
| 2016/0296916 A1* | 10/2016 | Kim .................... B01J 35/58 |

FOREIGN PATENT DOCUMENTS

| | | |
|---|---|---|
| JP | 2008208148 A | 9/2008 |
| WO | 2020/207926 A1 | 10/2020 |

\* cited by examiner

PROCESS FOR THE CONVERSION OF CARBON DIOXIDE

FIELD OF THE INVENTION

Embodiments of the present invention provide processes for the conversion of carbon dioxide, including carbon dioxide directly captured from the atmosphere, into synthesis gas, which can be useful for the production of organic molecules at industrially useful levels.

BACKGROUND OF THE INVENTION

Synthesis gas, which is also referred to as syngas, includes a mixture of hydrogen and carbon monoxide, optionally together with additional residual components such as carbon dioxide, nitrogen, methane, and water. Syngas has several uses including its use as a reactant feed to produce organic compounds such as hydrocarbons and alcohols.

Several methods have been used to synthesize syngas including its production from carbon dioxide. These processes include the conversion of carbon dioxide to carbon monoxide through the Reverse Water-Gas Shift (RWGS) reaction. The RWGS reaction is reversible and includes the reaction of carbon dioxide ($CO_2$) with hydrogen ($H_2$) to produce carbon monoxide (CO) and water ($H_2O$) in the presence of a catalyst. The produced carbon monoxide can then be combined with additional hydrogen to produce syngas, hydrogen can be removed, or the RWGS reaction can be run with excess $H_2$ to directly produce syngas with the removal of water from the product stream.

The RWGS reaction is a reversible reaction that can be operated essentially to equilibrium. The degree of $CO_2$ conversion depends on several factors including the feed gas composition, catalyst employed, the pressure, and the temperature at which the RWGS reaction takes place. Higher reaction temperatures generally lead to higher $CO_2$ conversion. For example, roughly about 55% conversion can be achieved at around 540° C., while about 80% conversion can be achieved at around 950° C.

Efforts to improve the efficiency of the RWGS reaction have been technologically important in extraterrestrial applications such as space travel. Given limited resources in most extraterrestrial applications, conservation of reactants, as well as energy, is critical to the usefulness of the application. For example, Whitlow et al., OPERATION, MODELING AND ANALYSIS OF THE REVERSE WATER GAS SHIFT PROCESS, AIP Conference Proceedings 654, 1116 (2003), proposes reaction techniques whereby water is pulled from the production stream and delivered as a reactant to an electrolysis step to thereby produce oxygen and hydrogen. And, unreacted carbon dioxide and hydrogen are recycled back to the RWGS reactor to ensure nearly complete conversion of the carbon dioxide reactant feed stream.

Environmental concerns over the level of atmospheric carbon dioxide have given rise to a desire to consume carbon dioxide and thereby potentially reduce the levels of atmospheric carbon dioxide. For example, U.S. Publ. No. 2007/0244208 proposes the conversion of carbon dioxide to liquid fuels. According to this process, hydrogen can be generated from water by electrolysis, and carbon dioxide can be captured from industrial processes. The carbon dioxide and hydrogen are reacted in RWGS reaction to produce carbon monoxide or other hydrocarbon precursors. It is suggested that the RWGS reaction can be run in recycle mode to 100% equilibrium conversion or alternatively the reaction can be driven by removal of water. It is also suggested that heat from other process steps in the overall process can be used to drive the RWGS reaction. While recycle or water removal are proposed, optionally together with heat integration, the preferred embodiments use condensation to remove carbon dioxide from the product stream and return it to the RWGS reaction.

Regardless of whether the operation is operated terrestrially or extra terrestrially, recycle of products from the product stream back to the RWGS reactor creates several complexities and drawbacks. For example, recycle systems require compressors, which introduce rotating equipment that can be unreliable and require maintenance, thereby inhibiting their efficient use within industrial-scale operations. Compressors also require power, which may result in undesirable inefficiencies and potential $CO_2$ or other emissions associated with power generation. Moreover, the processes proposed in the prior art focus on conservation or raw materials or formation of fuels rather than the consumption of carbon dioxide. Net $CO_2$ removal is now more desirable than ever and presents significant technological challenges, which are issues not confronted by the prior art.

Since the large-scale consumption of carbon dioxide remains desirable, there is a need for the continued development of efficient industrial-scale processes to achieve the consumption of carbon dioxide at levels that can impact atmospheric carbon dioxide levels.

SUMMARY OF THE INVENTION

One or more embodiments of the present invention provide a process for the production of syngas, the process comprising (i) reacting at least a portion of carbon dioxide with hydrogen within an initial reactor to produce an initial product stream including carbon monoxide, water, unreacted carbon dioxide, and unreacted hydrogen; and (ii) reacting at least a portion of the unreacted carbon dioxide and unreacted hydrogen within a reactor downstream of the first reactor to thereby produce a product stream including carbon monoxide, water, unreacted carbon dioxide, and unreacted hydrogen.

Other embodiments of the present invention provide a process for the production of syngas, the process comprising (i) providing a reactant stream including carbon dioxide; (ii) providing a reactant stream including hydrogen; (iii) combining the reactant stream including carbon dioxide with the reactant stream including hydrogen to form a mixed reactant stream; (iv) heating the mixed reactant stream to form a heated mixed reactant stream; (v) introducing the heated mixed reactant stream to an adiabatic reactor including a reverse water-gas shift catalyst; (vi) allowing the hydrogen and carbon dioxide to react within the adiabatic reactor to thereby form an initial product stream including carbon monoxide, water, hydrogen, and carbon dioxide; (vii) removing the initial product stream from the adiabatic reactor, where said initial product stream, upon exiting the adiabatic reactor, has a temperature T1; (viii) removing at least a portion of the water in the initial product stream from the initial product stream to form a water-lean initial product stream; (ix) introducing the initial product stream to a fired-tubular reactor including a reverse water-gas shift catalyst, where said fired-tubular reactor produces an exhaust stream including produced carbon dioxide and excess heat; (x) heating the product stream to a temperature T3 within the fired-tubular reactor, where T3 is greater than or equal to T1, to thereby react the carbon dioxide and hydrogen within the initial product stream to form a final product stream; (xi) routing at least a portion of the excess heat to said step of heating the mixed reactant stream to form a heated mixed reactant stream; and (xii) routing at least a portion of the produced carbon dioxide to said adiabatic reactor, or said fired-tubular reactor.

Yet other embodiments of the invention provide a process for the production of syngas, the process comprising (i) providing a reactant stream including carbon dioxide; (ii) providing a reactant stream including hydrogen; (iii) combining the reactant stream including carbon dioxide with the reactant stream including hydrogen to form a mixed reactant stream; (iv) heating the mixed reactant stream to form a heated mixed reactant stream; (v) introducing the heated mixed reactant stream to an initial adiabatic reactor including a reverse water-gas shift catalyst; (vi) allowing the hydrogen and carbon dioxide to react within the initial adiabatic reactor to thereby form an initial product stream including carbon monoxide, water, hydrogen, and carbon dioxide; (vii) removing the initial product stream from the initial adiabatic reactor, where said initial product stream, upon exiting the initial adiabatic reactor, has a temperature T1; (viii) removing at least a portion of the water in the initial product stream from the initial product stream to form a water-lean initial product stream; (ix) heating the water-lean initial product stream to form a heated water-lean initial product stream; (x) introducing the heated water-lean initial product stream to a downstream adiabatic reactor including a reverse water-gas shift catalyst; (xi) allowing the hydrogen and carbon dioxide to react within the downstream adiabatic reactor to thereby form an intermediary product stream including carbon monoxide, water, hydrogen, and carbon dioxide; (xii) removing the intermediary product stream from the downstream adiabatic reactor, where said intermediary product stream, upon exiting the downstream adiabatic reactor, has a temperature T2; (xiii) removing at least a portion of the water in the intermediary product stream to form a water-lean intermediary product stream; (xiv) optionally heating the water-lean intermediary product stream to form a heated, water-lean intermediary product stream at temperature T02; (xv) optionally Introducing the heated, water-lean intermediary product stream to a downstream adiabatic reactor including a reverse water-gas shift catalyst and allowing the carbon dioxide and hydrogen in the heated, water-lean intermediary product stream to react and thereby ultimately form a final intermediary product stream; (xvi) introducing the intermediary product stream or the final intermediary product stream to a fired-tubular reactor including a reverse water-gas shift catalyst, where said fired-tubular reactor produces an exhaust stream including produced carbon dioxide and excess heat; (xvii) heating the intermediary or final intermediary product stream to a temperature T3 within the fired-tubular reactor, where T3 is greater than or equal to T2, and where T3 is greater than or equal to T1, to thereby react the carbon dioxide and hydrogen within the intermediary product stream or the final intermediary product stream to form a final product stream; (xviii) routing at least a portion of the excess heat to said step of heating the mixed reactant stream to form a heated mixed reactant stream or to said step of heating the initial product stream to form a heated initial product stream; and (xix) routing at least a portion of the produced carbon dioxide to said adiabatic reactor, said downstream adiabatic reactor, or said fired-tubular reactor.

Still other embodiments of the invention provide a RWGS system comprising (i) an initial RWGS reactor including a reverse water-gas shift catalyst, said RWGS reactor adapted to facilitate the reaction of hydrogen and carbon dioxide to thereby form an initial product stream including carbon monoxide, water, hydrogen, and carbon dioxide; (ii) downstream of said initial RWGS reactor, a water removal unit for removing water from the initial product stream; (iii) optional one or more intermediary RWGS reactors, positioned in series, downstream of said initial RWGS reactor, each optional intermediary RWGS reactor including a water-gas shift catalyst, said optional intermediary reactors adapted to facilitate the reaction of hydrogen and carbon dioxide to form intermediary product streams and ultimately form an final intermediary product stream including carbon monoxide, water, hydrogen, and carbon dioxide; (iv) optional a water removal units for removing water from the intermediary product streams and final intermediary product stream; and (v) a final RWGS reactor downstream of and positioned in series to said initial RWGS reactor and said optional one or more intermediary RWGS reactors, said final RWGS reactor including a water-gas shift catalyst, said final RWGS reactor adapted to facilitate the reaction of hydrogen and carbon dioxide to thereby form a final product stream including carbon monoxide, water, hydrogen, and carbon dioxide.

DETAILED DESCRIPTION OF ILLUSTRATIVE EMBODIMENTS

Figure 1:
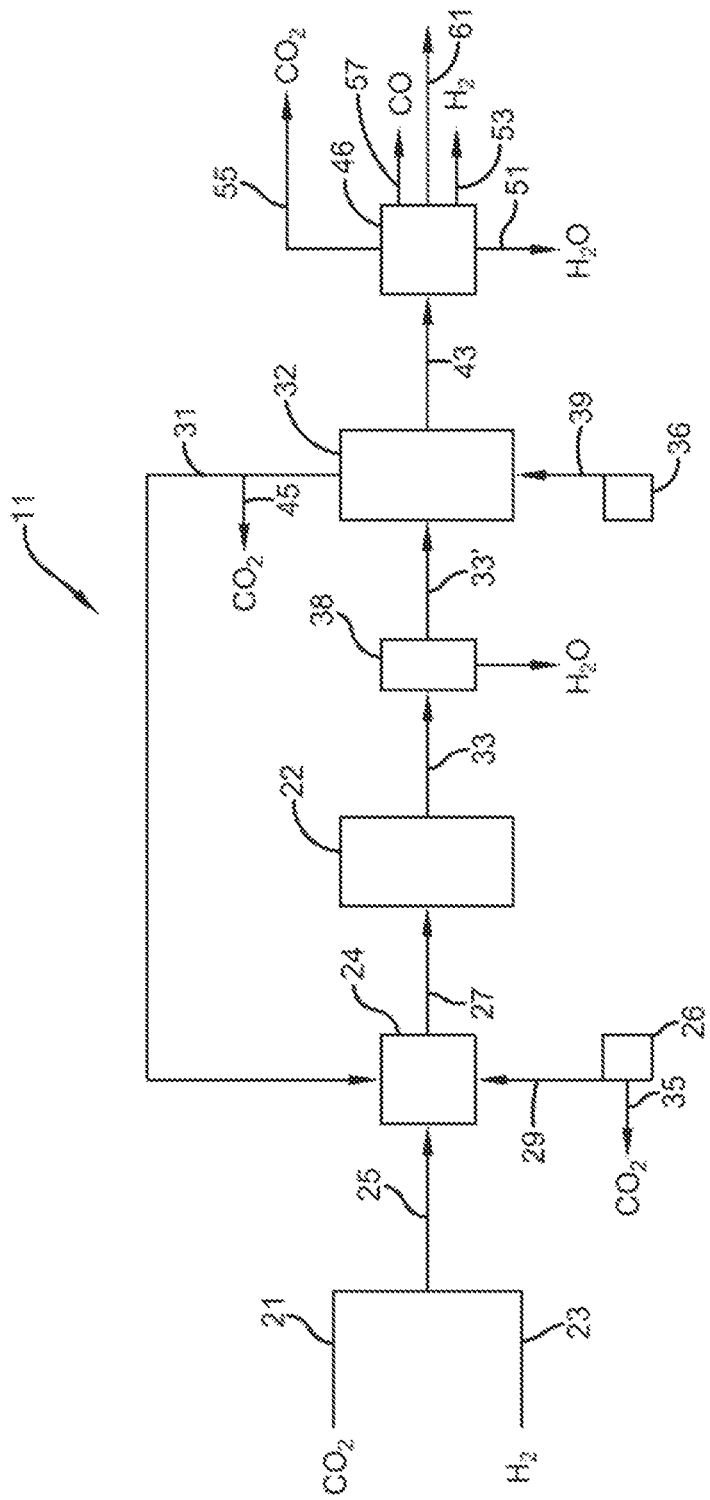
FIG. 1 is a schematic view of a two-step RWGS process according to embodiments of the invention.

Embodiments of the invention are based, at least in part, on the discovery of an industrially significant process whereby carbon dioxide is converted to carbon monoxide at increased conversion rates while maintaining an overall balance of reaction efficiency. The process takes advantage of the Reverse Water-Gas Shift (RWGS) reaction within a multistage reaction scheme that optionally includes both heat integration and water removal to achieve overall process efficiency. And, the reaction conditions are tailored at each stage to achieve overall reaction efficiencies. Thus, while the prior art proposes recycling unreacted carbon dioxide back to the RWGS reactor to drive complete conversion of the carbon dioxide, the present invention achieves desirable efficiencies at industrially significant levels. Further, when coupled with heat integration and/or separation of components between the reaction steps, further overall efficiencies can be realized.

Process Overview

Two-Step Embodiment

A process according to the present invention can be described with reference to FIG. 1, which shows reverse water-gas shift (RWGS) process 11 including an initial RWGS reaction step 22, which may also be referred to as first RWGS reaction step 22, followed in series by a final RWGS reaction step 32. Carbon dioxide ($CO_2$) stream 21 and hydrogen ($H_2$) stream 25 may be combined to form a mixed reactant stream 25 that is then heated in heating step 24 (e.g. within a heat exchanger). Heated mixed reactant stream 27 is then routed from first heating step 24 to first RWGS reaction step 22, where $CO_2$ and $H_2$ are reacted to produce carbon monoxide (CO) and water ($H_2O$) in the presence of catalyst (e.g. within an adiabatic reactor).

Heat may be supplied to heating step 24 from one or more heat sources. For example, heat 29 may be supplied from a dedicated heat source 26. Alternatively, or in addition to dedicated heat source 26, heat from downstream process steps may be received by heating step 24. For example, as shown in FIG. 1, and which will be described in greater detail herein below, excess heat within exhaust stream 31 from final RWGS reaction step 32 can be routed to heating step 24. In those optional embodiments where carbon dioxide is produced in the generation of heat, such as at heat source 26, the produced carbon dioxide can be routed back to first RWGS reaction step 22 where it can be at least partially converted to carbon monoxide. For example, stream 35 containing produced carbon dioxide can be combined with carbon dioxide feed stream 21, mixed stream 25, or directly introduced to reaction step 22. Alternately, the produced carbon dioxide may be routed to the final RWGS reaction step 32, or to an intermediate point in the process for conversion to carbon monoxide via a RWGS reaction.

The CO and $H_2O$ products, together with any unreacted reactants, are routed from first RWGS reaction step 22 as product stream 33 to second RWGS reaction step 32. In one or more embodiments, product stream 33 may undergo water removal within a water removal step 38 prior to final RWGS reaction step 32, whereby water removal step 38 produces a water-lean product stream 33'. Water-lean product stream 33' may then be introduced to final RWGS reaction step 32.

Heat 39 may be supplied to final RWGS reaction step 32 from a heat source 36, which produces an exhaust stream 31 that includes heat not consumed by reaction step 32 (i.e. excess heat) and optionally produced carbon dioxide. As noted above, excess heat from RWGS reaction step 32 may be supplied to upstream steps, such as heating step 24, via exhaust stream 31 as shown in FIG. 1. Although not shown, excess heat within exhaust stream 31 may be used to preheat product stream 33, 33' prior to entry into final RWGS reaction step 32. As with heat source 26, the produced carbon dioxide within exhaust stream 31 can be routed back to upstream RWGS reactions (e.g. first RWGS reaction step 22). For example, a stream 45 containing produced carbon dioxide from exhaust stream 31 can be combined with carbon dioxide feed stream 21, mixture 25, or fed directly to reaction step 22.

While FIG. 1 shows final RWGS reaction step 32 with heat 39 directly added to reaction step 32, it will be appreciated that in other embodiments, final RWGS reaction step may include an arrangement similar to that shown relative to reaction step 22 where heating takes place prior to entry into the reactor. Again, the skilled person will understand that preheating of the stream or direct heating of the reactant stream during the reaction step may depend on the type of reactor chosen (e.g. adiabatic reactor or non-adiabatic reactor).

$CO_2$ and $H_2$ within product stream 33 (or water-lean stream 33') are reacted within final RWGS reaction step 32 to produce CO and $H_2O$, which together with any unreacted reactants exit final RWGS reaction step 32 as final product stream 43. Final product stream 43 may undergo one or more separations within, for example, separation step 46. For example, separation step 46 may remove water via water stream 51. In addition to or in lieu of water removal, at least a portion of the hydrogen within final product stream can be removed (e.g. by way of membrane) to form a hydrogen-rich stream 53. Likewise, in addition to or in lieu of the separation of water and/or hydrogen, carbon dioxide can optionally be separated to produce carbon dioxide-rich stream 55, and/or carbon monoxide can optionally be separated to produce carbon monoxide-rich stream 57.

In one or more embodiments, final product stream 43 is a syngas stream. Those skilled in the art appreciate that separations and/or purification can be performed on product stream 43 to produce altered syngas stream 61. For example, components can be recovered (e.g. recovery of $H_2O$, $H_2$, CO, and/or $CO_2$), purifications can take place, and/or the ratio of the components can be manipulated to produce altered syngas stream 61. In one or more embodiments, carbon dioxide contained in stream 43, for example after a separation step to form carbon dioxide rich stream 55, can be routed back to upstream RWGS reaction steps to convert at least a portion of the carbon dioxide to carbon monoxide. For example, carbon dioxide-rich stream 55 can be combined with carbon dioxide feed stream 21. Alternately, the carbon dioxide-rich stream may be routed back to final RWGS reaction step 32, or to an intermediate point in the process for conversion of the carbon dioxide to carbon monoxide via RWGS reaction. It will be appreciated that while FIG. 1 shows separation step 46 as a single step, multiple separation steps may be present to accomplish the desired separations and/or purifications.

Multi-Step Process

In one or more embodiments, the process of the present invention includes three or more reaction steps. In one or more embodiments, the final step is operated at a higher temperature than the preceding reaction steps. The reaction steps preceding the final RWGS reaction step, which include the initial RWGS reaction step and any intermediary RWGS reaction steps, may each be conducted at the same temperature. In other embodiments, one or more of the intermediary RWGS reaction steps are conducted at a temperature higher than the initial RWGS step. In particular embodiments, each intermediary RWGS reaction step is conducted at a higher temperature than the preceding step. In yet other embodiments, each step of the multi-step process is randomly operated relative to temperature. In one or more embodiments, water is removed from the product stream exiting one or more of the RWGS reaction steps prior to delivery to the subsequent reaction step.

Figure 2:
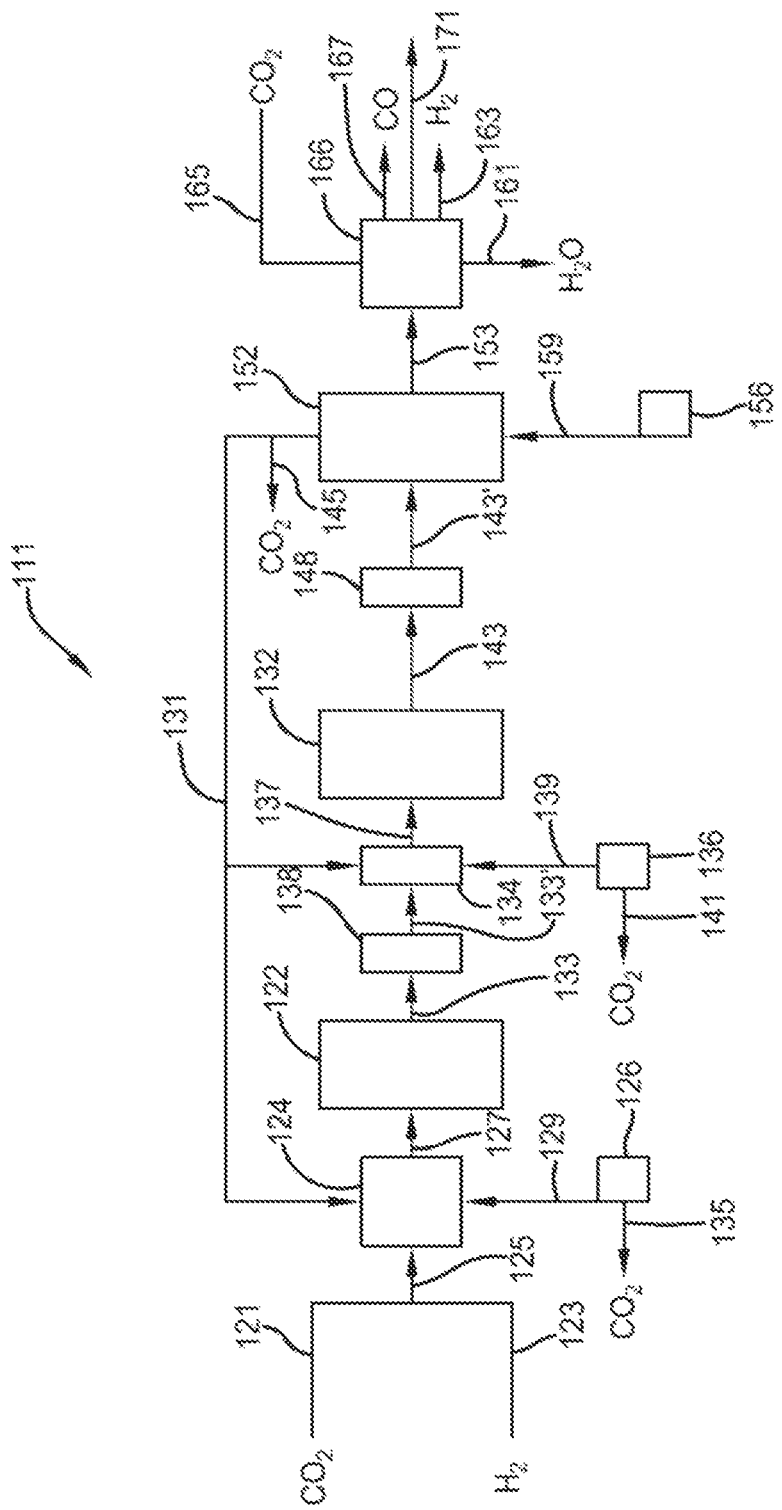
FIG. 2 is a schematic view of a multi-step RWGS process according to embodiments of the invention.

An exemplary multi-stage process can be described with reference to FIG. 2, which shows a three-step reaction process 111 including an initial RWGS reaction step 122, an intermediary RWGS reaction step 132, and a final RWGS reaction step 152. Although not shown, process 111 may include greater than 1, in other embodiments greater than 3, in other embodiments greater than 10, in other embodiments greater than 20, and in other embodiments greater than 100 intermediary RWGS reaction steps. In these or other embodiments, process 111 may include less than 100, in other embodiments less than 30, and in other embodiments less than 10 intermediary RWGS reaction steps. In one or more embodiments, the process of the present invention may include from about 1 to about 100, in other embodiments from about 2 to about 30, and in other embodiments from about 3 to about 10 intermediary RWGS reaction steps.

With reference again to FIG. 2, $CO_2$ stream 121 and $H_2$ stream 123 are combined into mixed reactant stream 125, heated at heating step 124 to form a heated stream 127, and routed to initial RWGS reaction step 122, where at least some of the $CO_2$ and $H_2$ is converted to CO and $H_2O$ in the presence of catalyst to form product stream 133. As with the embodiments of FIG. 1, heating step 124 and reaction step 122 may be combined into a single step depending upon the type of reactor employed. Also, it will be understood that, in one or more embodiments, mixed reactant stream 125 (as well as reactant stream 25 above) can be sourced directly, and therefore $CO_2$ stream 121 and $H_2$ stream 123 may optionally not exist.

Heating step 124 may receive heat from one or more heat sources. For example, heat 129 may be produced from a dedicated heat source 126. Alternatively, or in addition to dedicated heat source 126, heat from downstream process steps may be received by heating step 124. For example, as shown in FIG. 1, excess heat within exhaust stream 131 is received from final RWGS reaction step 152. In another example (not shown), exhaust heat may be received from an intermediary RWGS reaction step (e.g. step 132) or intermediary heating source. In those embodiments where carbon dioxide is produced in the generation of heat, such as at heat source 126, the produced carbon dioxide 135 can be routed back to first RWGS reaction step 122 where it can be at least partially converted to carbon monoxide. For example, produced carbon dioxide can be combined with carbon dioxide feed stream 121, mixed stream 125, or directly introduced to reaction step 122. Alternately, produced carbon dioxide may be routed to the final RWGS reaction step 152, or to an intermediate point in the process for conversion to carbon monoxide via RWGS reaction.

In one or more embodiments, product stream 133 from initial RWGS reaction step 122 may optionally be routed to an optional water removal step 138 to produce water-lean product stream 133', which is then routed to an intermediary heating step 134 to form heated stream 137. Heat 139 may be supplied to heating step 136 from one or more heat sources. For example, heat 139 may be supplied from a dedicated heat source 136. Alternatively, or in addition to dedicated heat source 136, heat may be routed from other process steps. For example, as shown in FIG. 2, and which will be described in greater detail herein below, excess heat within exhaust stream 131 from final RWGS reaction step 152 can be routed to heating step 134. In those embodiments where carbon dioxide is produced in the generation of heat, such as at heat source 136, produced carbon dioxide 141 can be routed back to first RWGS reaction step 122 where it can be at least partially converted to carbon monoxide. For example, the produced carbon dioxide can be combined with carbon dioxide feed stream 121, mixed stream 125, or directly introduced to reaction step 122. Alternately, the produced carbon dioxide may be routed to the final RWGS reaction step 152, or to an intermediate point in the process for conversion to carbon monoxide via RWGS reaction. As with the reaction step 122 and heating step 124, heating step 134 and reaction step 132 may be combined into a single step depending upon the type of reactor employed.

Heated stream 137 is routed from heating step 134 to an intermediary RWGS reaction step 132, where at least some of the $CO_2$ and $H_2$ within heated stream 137 is converted to CO and $H_2O$ to form intermediary product stream 143. Intermediary product stream 143 exiting intermediary RWGS reaction step 132 can optionally be routed to one or more additional intermediary RWGS reaction steps (not shown). In one or more embodiments, these one or more intermediary RWGS reaction steps are positioned in series. As the process stream proceeds downstream through the one or more intermediary RWGS reaction steps, the process stream may undergo one or more water removal steps (not shown) prior to entering subsequent intermediary RWGS reaction steps. Also, depending on the type of rector employed, the one or more intermediary RWGS reaction steps may include preheating the stream prior to entering the reaction step, or the stream may be simultaneously heated during the intermediary RWGS reaction step.

Ultimately, the intermediary product stream from the one or more intermediary RWGS reaction steps (e.g. stream 143) is routed to a final RWGS reaction step 152. Prior to final RWGS reaction step 152, stream 143 may undergo an optional water removal step 148 to form water-depleted product stream 143'. Final RWGS reaction step may receive heat 159 from a heat source 156 and produce exhaust stream 131, which may include excess heat and/or produced carbon dioxide. For example, excess heat within exhaust stream 131 from final RWGS reaction step 152 can be routed to upstream process steps such as heating steps 124 and/or 134. Also, excess heat within exhaust stream 131 can be routed to any of the preceding reaction steps or can used to preheat any of the upstream streams. Where carbon dioxide is produced in the generation of heat 159, such as at heat source 156, produced carbon dioxide 145 can be routed to any of the RWGS reaction steps where it can be at least partially converted to carbon monoxide. For example, the produced carbon dioxide can be combined with carbon dioxide feed stream 121, mixed stream 125, or directly introduced to one of the reaction steps. Alternately, the produced carbon dioxide may be routed to the final RWGS reaction step 152, or to an intermediate point in the process for conversion to carbon monoxide via RWGS reaction.

Within final RWGS reaction step 152, $CO_2$ and $H_2$ within product stream 143 are reacted to further produce CO and $H_2O$, which together with any unreacted reactants exit final RWGS reaction step 152 as final product stream 153. Final product stream 153 may undergo one or more separations within, for example separation step 166. For example, separation step 166 may remove water via water stream 161. In addition to or in lieu of water removal, at least a portion of the hydrogen within final product stream 153 can be removed to form a hydrogen-rich stream 163. Likewise, in addition to or in lieu of separation of water and/or hydrogen, carbon dioxide can optionally be separated to produce carbon dioxide-rich stream 165, and/or carbon monoxide-rich stream 167.

In one or more embodiments, final product stream 153 is a syngas stream. Those skilled in the art appreciate that separations and/or purifications can be performed on product stream 153 to produce altered syngas stream 171. For example, components can be recovered (e.g. recovery of CO, $CO_2$, $H_2$, and/or $H_2O$), purifications can take place, and/or the ratio of components can be manipulated to produce altered syngas stream 171. In one or more embodiments, carbon dioxide contained within stream 153, for example after a separation step to form carbon dioxide-rich stream 165, can be routed back to upstream RWGS reaction steps to convert at least a portion of the carbon dioxide to carbon monoxide. For example, carbon dioxide-rich stream 165 can be combined with carbon dioxide feed stream 121. Alternately, carbon dioxide-rich stream 165 may be routed back to final RWGS reaction step 152, or to an intermediate point in the process for conversion of the carbon dioxide to carbon monoxide via RWGS reaction. It will be appreciated that while FIG. 2 shows separation step 166 as a single step, multiple separation steps may be present to accomplish the desired separations and/or purifications.

Reactant Streams

In one or more embodiments, the process of the present invention involves providing to the initial RWGS reaction step an appropriate feed rate of carbon dioxide and hydrogen to provide at least one mole of hydrogen to one mole of carbon dioxide within the initial RWGS reaction step. In these or other embodiments, an excess of hydrogen is fed to the initial RWGS reaction step. For example, the feed of hydrogen and carbon dioxide can be set to provide the initial RWGS reaction step with a molar ratio of hydrogen to carbon dioxide of greater than 1:1, in other embodiments greater than 1.5:1, in other embodiments greater than 2.5:1, and in other embodiments greater than 5:1. In one or more embodiments, the hydrogen and carbon dioxide feeds provide the initial RWGS reaction step with a molar ratio of hydrogen to carbon dioxide of from about 1:1 to about 10:1, in other embodiments from about 1.3:1 to about 5:1, in other embodiments from about 1.5:1 to about 4:1, and in other embodiments from about 2.5:1 to about 3.5:1.

In one or more embodiments, the carbon dioxide reactant stream (e.g. stream 21, 121) feeding the initial RWGS reaction step (or feeding any preliminary mix step where carbon dioxide and hydrogen are combined) includes greater than 50 mol %, in other embodiments greater than 85 mol %, in other embodiments greater than 90 mol %, in other embodiments greater than 95 mol %, in other embodiments greater than 98 mol %, and in other embodiments greater than 99 mol % carbon dioxide. In one or more embodiments, the carbon dioxide reactant stream that is fed to the initial RWGS reaction step (or combined with the hydrogen reactant stream) includes from about 50 mol % to about 100 mol %, in other embodiments from about 75 mol % to about 99.9 mol %, and in other embodiments from about 99 mol % to about 100 mol % carbon dioxide.

In one or more embodiments, the hydrogen reactant stream (e.g. stream 23, 123) feeding the initial RWGS reaction step (or feeding any preliminary mix step where carbon dioxide and hydrogen are combined) includes greater than 50 mol %, greater than 75 mol %, in other embodiments greater than 85 mol %, in other embodiments greater than 90 mol %, in other embodiments greater than 95 mol %, in other embodiments greater than 98 mol %, and in other embodiments greater than 99 mol % hydrogen. In one or more embodiments, the hydrogen reactant stream that is fed to the initial RWGS reaction step (or combined with the carbon dioxide stream) includes from about 50 to about 100 mol %, in other embodiments from about 75 to about 99.9 mol %, and in other embodiments from about 99 mol % to about 100 mol % hydrogen.

In one or more embodiments, the reactant stream introduced to the initial RWGS reaction step 22, 122, which may include mixed stream 25, 125, as well as heated streams 27, 127, (i.e. the reactants reacted within the initial reaction step), includes at least 50 mol %, in other embodiments at least 75 mol %, in other embodiments at least 90 mol %, and in other embodiments at least 95 mol % carbon dioxide and hydrogen combined. In these or other embodiments, the reactant stream introduced to the initial RWGS reaction step 22, 122, is substantially devoid of methane, which includes that amount or less that would otherwise have an appreciable impact on the practice of this invention. In one or more embodiments, the reactant stream introduced to the initial RWGS reaction step 22, 122, is devoid of methane. In one or more embodiments, the reactant stream introduced to the initial RWGS reaction step 22, 122, includes less than 20 mol %, in other embodiments less than 10 mol %, in other embodiments less than 5 mol %, in other embodiments less than 2 mol %, and in other embodiments less than 1 mol % methane.

Similarly, it is desirable to minimize the production of methane within the RWGS reactions. For example, the product streams produced may include less than 20 mol %, in other embodiments less than 10 mol %, in other embodiments less than 5 mol %, in other embodiments less than 2 mol %, and in other embodiments less than 1 mol % methane. In one or more embodiments, the product stream is substantially devoid of methane, and in other embodiments the product stream is devoid of methane.

RWGS Process Conditions

In one or more embodiments, first heating step 24, 124 produces heated mixed reactant stream 27, 127 (which will be the heat of the stream entering the first RWGS reaction step 22, 122) with a temperature of greater than 350° C., in other embodiments greater than 450° C., in other embodiments greater than 500° C., and in other embodiments greater than 525° C. In these or other embodiments, first heating step 24, 124 produces heated mixed reactant stream 27, 127 with a temperature of less than 700° C., in other embodiments less than 650° C., and in other embodiments less than 600° C. In one or more embodiments, first heating step 24, 124 produces heated mixed reactant stream 27, 127 with a temperature of from about 450 to about 700° C., in other embodiments from about 500 to about 650° C., and in other embodiments from about 525 to about 600° C. Similarly, any downstream intermediary reaction steps that include preheating of the intermediary reactant stream may be heated to similar temperatures.

In one or more embodiments, the initial RWGS reaction step (22, 122) takes place adiabatically. In these or other embodiments, the initial RWGS and one or more of the intermediary RWGS reaction steps (132) takes place adiabatically. In particular embodiments, each of the first RWGS (22, 122) and intermediary RWGS (132) reaction steps take place adiabatically. In these or other embodiments, the final RWGS step (32, 152) takes place adiabatically.

For purposes of this specification, the temperature at which any of the RWGS reaction steps take place is quantified or characterized by the temperature of the product stream immediately exiting the reaction step (e.g. the outlet temperature of a reactor in which the reaction step takes place).

In one or more embodiments, initial reaction step 22, 122 takes place at a temperature of greater than 300° C., in other embodiments greater than 450° C., in other embodiments greater than 500° C., and in other embodiments greater than 525° C. In these or other embodiments, initial reaction step 22, 122 takes place at a temperature of less than 1000° C., in other embodiments less than 800° C., in other embodiments less than 650° C., and in other embodiments less than 600° C. In one or more embodiments, initial reaction step 22, 122 takes place at a temperature of from about 400 to about 1200° C., in other embodiments from about 300 to about 1000° C., in other embodiments from about 450 to about 800° C., in other embodiments from about 500 to about 750° C., and in other embodiments from about 525 to about 600° C.

In one or more embodiments, final RWGS reaction step 32, 152 takes place at a temperature of greater than 500° C., in other embodiments greater than 800° C., in other embodiments greater than 850° C., and in other embodiments greater than 900° C. In these or other embodiments, final RWGS reaction step 32, 152 takes place at a temperature of less than 1200° C., in other embodiments less than 1100° C., and in other embodiments less than 1000° C. In one or more embodiments, final reaction step 32, 152 takes place at a temperature of from about 500 to about 1200° C., in other embodiments from about 800 to about 1200° C., in other embodiments from about 850 to about 1100° C., and in other embodiments from about 900 to about 1000° C.

In one or more embodiments, optional water removal step 38 (as well as 138, 148) removes greater than 10%, in other embodiments greater than 25%, and in other embodiments greater than 50% of the water within product stream 33. In these or other embodiments, water removal step 38 removes less than 100%, in other embodiments less than 90%, and in other embodiments less than 70% of the water within product stream 33. In one or more embodiments, water removal step 38 removes from about 10 to about 100%, in other embodiments from about 25 to about 90%, and in other embodiments from about 50 to about 90% of the water within product stream 33, 133, 143.

The RWGS process, including any individual steps thereof, may take place over a wide range of pressures including from atmospheric pressure to about 550 psi and even 1000 psi or higher. Typical reactor pressures may be chosen to match downstream uses or to minimize compression. In one or more embodiments, the RWGS process is operated at a pressure of from about 400 to about 600 psi.

Heating Devices

In those RWGS steps that take place adiabatically, the reactant stream can be preheated, such as at heating steps 24, 124, 134, using appropriate equipment such as, but not limited to, heat exchangers.

Those skilled in the art can readily determine, without undue calculation or experimentation, the appropriate design configurations and material equipment requirements for the heating devices (e.g. heat exchangers) based upon the desired process conditions. For example, the desired temperature of the reaction step can dictate the materials that can be used to construct the heating devices, or portions thereof.

Heat Energy to RWGS Reactions

Heat delivered to the reactant streams in the adiabatic reaction steps or directly to the reaction step in the non-adiabatic reaction steps can derived from a variety or heating sources. For example, heat can be supplied by the combustion of fossil fuels, such as natural gas. Alternatively, heat can be supplied by electrical energy. Electrical energy, for example, can derive from a variety of sources such as nuclear power, wind power, solar power, hydropower, and the combustion of fuel optionally with $CO_2$ capture. Alternately, heat can be supplied by the combustion of a carbon-free fuel, for example hydrogen, which can produce energy without generating carbon dioxide.

As indicated above, where the one or more heat sources (e.g. heat sources 126, 136, 156) used to provide heat energy the RWGS reaction steps generates carbon dioxide in the generation of heat, the carbon dioxide that is generated can optionally be captured and routed back as a reactant to the RWGS process (e.g. routed back to carbon dioxide streams 21, 121). In one or more embodiments, at least 20%, in other embodiments at least 50%, in other embodiments at least 70%, in other embodiments at least 85%, and in other embodiments at least 90% of the carbon dioxide produced in the generation of heat (e.g. combustion of fuel such as natural gas) for the RWGS reaction steps of this invention is captured and returned to the process as a reactant.

RWGS Reactors

The RWGS reaction steps of the present invention can be conducted in vessels that allow for the reaction to take place in the presence of a catalyst while providing the ability to efficiently transfer heat to the reaction. For example, the reaction may take place within fixed bed reactors, which may also be referred to as packed bed reactors. Where the RWGS reaction takes place adiabatically, the reactor may include an optionally insulated packed bed vessel or tank. Where the RWGS reaction takes place non-adiabatically, the reactor may include a heated packed bed reactor, for example a fired-tubular packed bed reactor, radiant heated packed bed reactor, electrically heated packed bed reactor, microwave heated packed bed reactor, and convectively heated packed bed reactor.

Those skilled in the art can readily determine, without undue calculation or experimentation, the appropriate design configurations and material equipment requirements for the reactors based upon the desired process conditions. For example, the desired temperature of the reaction step can dictate the materials that can be used to construct the reaction vessel, or portions thereof (e.g. reaction tubes). For example, when a low-temperature RWGS reaction is desired (e.g. reactions at temperatures below about 800° C.), then the reactor components may be constructed of stainless steel or other metals or alloys that can withstand temperatures up to about 800° C. On the other hand, when high-temperature RWGS reactions are desired (e.g. reactions above about 800° C.), then the reactor components may be constructed of high-grade metals or alloys, such as nickel alloys, that can withstand temperatures up to about 1200° C.

The overall process design advantageously allows a portion of the required heat of reaction (i.e. $\Delta Hr$) necessary to drive the RWGS reaction to be supplied from a lower energy system (i.e. a first low-temperature reaction step), which reduces the amount of energy that must be transferred to the reaction within the high-temperature RWGS reaction step, which advantageously operates at a higher temperature and thereby drives further $CO_2$ conversion. Thus, by operating the high-temperature RWGS reaction step at elevated temperatures, $CO_2$ conversion of the overall process can be driven beyond those levels achieved at lower temperatures, while not relying on the high-temperature RWGS reaction step to provide all heat transfer requirements for the overall conversion reaction. As a result, the characteristics of the high-temperature RWGS reaction step can advantageously be tailored to accommodate less duty, especially heat transfer duty, which provides overall efficiencies, especially in terms of capital cost requirements. For example, the low-temperature RWGS reaction steps can be conducted in vessels constructed of materials that are not required to withstand the extremely high temperatures of the high-temperature RWGS reaction step. And, the reactor design for the high-temperature RWGS reaction step can be scaled back given that the high temperature heat transfer requirements are less than if only one RWGS reaction step was involved in the process.

Catalysts

As indicated above, both the high-temperature (e.g. above about 800° C.) and low-temperature (e.g. from about 350 to about 800° C.) RWGS reactions are catalytically driven. Practice of the present invention is not, however, limited to a specific catalyst system so long as the catalyst promotes or otherwise facilitates the reverse water-gas shift reaction. Reference may therefore be made to reverse water-gas shift catalyst. Those having skill in the art appreciate that reaction conditions, especially for any given RWGS reaction, can impact the catalytic system of choice, and those skilled in the art will be able to readily select an appropriate catalyst without undue experimentation or calculation.

In one or more embodiments, a fixed bed catalyst system is employed. As the skilled person appreciates, these systems include catalytic materials disposed on an appropriate support material. Useful support materials are generally known in the art and include those materials that can be appropriately packed in the reactor (e.g. tube reactors).

Useful catalysts include high-temperature shift catalysts, which are generally known in the art and are useful at the higher temperatures that the reverse shift reactions take place (e.g. generally above 400° C.). An exemplary high-temperature reverse water-gas shift catalyst compositionally includes iron oxide, chromium oxide, and optionally magnesium oxide. Another example is a catalyst based on oxides of manganese and cesium and/or lanthanum series metals, optionally with carbonates or oxycarbonates in addition to or lieu of the oxides, and optionally together with platinum.

Other high-temperature shift catalysts include those disclosed in U.S. Publ. Nos. 2017/0197829, 2015/0080482, 2010/0105962, 2003/0113244, and 2007/0142482, which are incorporated herein by reference.

Water Removal Techniques

As indicated above, practice of the present invention may include one or more steps for the removal of water from a product stream. Several techniques can be used. For example, condensation of the water out of the product stream can be accomplished by condensation techniques including removal of heat from the product stream.

In other embodiments, water is removed without the removal of a significant amount of heat energy from the product stream. For example, in one or more embodiments, water is removed by membrane separation. Those skilled in the art appreciate that these membrane systems may require pressure drop across the membrane, use of permeate sweep gas to affect water removal, and/or temperature adjustment. In other embodiments, adsorption techniques may be employed. For example, solid sorbents, metal oxide frameworks (MOF), and zeolitic imidazolate frameworks (ZIF) may be employed. The skilled person will appreciate that these absorbent systems may require temperature and/or pressure adjustments.

In one or more embodiments, the water is removed by reaction with methane via the steam reforming reaction, which may also be referred to as steam methane reforming (SMR).

Carbon Dioxide Sources

In one or more embodiments, carbon dioxide can be obtained from a variety of point sources. In one or more embodiments, the carbon dioxide stream can derive from carbon dioxide capture processes that can be located at a variety of point sources such as combustion operations and various industrial operations. Combustion processes can include, but are not limited to, coal or gas power plants, vehicle operation, and incineration or waste disposal. Industrial operations include, but are not limited to, aluminum smelting, ammonia production, hydrogen production, refining, cement production, iron smelting, ferro-alloy production, steel production, lime production, and glass production. Carbon dioxide capture technology may include, but are not limited to, absorption, adsorption, membrane separation, and cryogenic separation. For example, carbon dioxide can be absorbed using amine-based technologies.

In other embodiments, carbon dioxide can be captured from atmospheric air (i.e. not at a particular point source). These techniques may include direct air capture (DAC), which captures carbon dioxide directly from ambient air. Useful techniques include liquid solvent absorption using amine or caustic solutions. Other techniques include anionic exchange polymer resins, metal-organic frameworks, adsorption, and membrane separation.

In particular embodiments, DAC using potassium hydroxide solutions is used to provide the carbon dioxide stream. For example, a useful DAC process is described in Keith et al., A Process for Capturing CO2 from the Atmosphere, Joule (2018). Similar processes are also described in U.S. Publ. Nos. 2017/0354925, 2014/0271379, 2019/0344217, 2019/0359894, 2019/0336909, which are incorporated herein by reference.

Since the reverse water-gas shift (RWGS) reaction processes of the present invention can be designed to achieve an attractive net carbon dioxide consumption, the processes of the present invention can be advantageously combined with direct air capture techniques to thereby provide overall industrially useful carbon dioxide consumption levels.

Hydrogen Sources

In one or more embodiments, the hydrogen stream may be supplied by an electrolysis process wherein water undergoes electrolysis to produce hydrogen and oxygen. Electricity requirements for the electrolysis process may be provided from alternative and renewable energy sources such as geothermal sources, solar power, wind energy, hydro-power, nuclear power, combustion of waste, ocean thermal- or kinematic-power, or from off-peak power grid supplies.

In other embodiments, the hydrogen stream may be supplied by reforming; for example by steam reforming of natural gas and autothermal reforming of natural gas.

In other embodiments, the hydrogen stream may be supplied from an off gas or waste gas from another process; for example from a hydrotreating process, hydrocracking process, or other industrial process which uses or produces hydrogen.

Product Stream Uses

In one or more embodiments, the carbon monoxide produced by practice of this invention can be used as a building block for the production of various fuels and chemicals.

In one or more embodiments, the product stream produced by practice of the present invention includes a mixture of carbon monoxide and hydrogen, which may be referred to as synthesis gas or syngas. For example, the molar ratio of carbon monoxide to hydrogen may be from about 0.5:1 to about 5:1 or greater, in other embodiments from about 1:1 to about 3:1, and in other embodiments from about 1.5:1 to about 2.5:1. As those skilled in the art will appreciate, the feed rate of the hydrogen relative to the carbon dioxide into the process of this invention, as well as the configured process (e.g. number of stages), operating conditions (e.g. temperatures of stages, water removal), and post-synthesis manipulation of the raw syngas stream can be tailored to provide a product stream with the desired molar ratio of carbon monoxide to hydrogen.

In one or more embodiments, the product stream produced by the process of the present invention is a syngas stream that can be subjected to a Fischer-Tropsch process to produce hydrocarbons such as diesel, gasoline, naphtha, waxes, LPGs, or methane.

In other embodiments, the product stream produced by the process of the present invention is a syngas stream that is used in the production of methanol (i.e. methanol synthesis) or other alcohol synthesis.

The system for conducting the processes of the present invention, which system generally includes RWGS reactors positioned in series, together with optional heating and water removal units positioned between the RWGS reactors, can be constructed by those having skill in the art without undue experimentation or calculation. In conjunction therewith, the skilled person will be able to readily select appropriate equipment, such as pipes or other conduits, to place one or more elements of the system in fluid communication with each other (e.g. transfer materials between the various reactors or recycle certain materials within the system) and/or to place one or more elements of the system in thermal communication with each other (e.g. transfer heat between the various process steps). The skilled person will also be able to readily heat and cool the various streams, and take appropriate measurements thereof in accordance with practice of the present invention.

In order to demonstrate the practice of the present invention, the following examples have been simulated. The examples should not, however, be viewed as limiting the scope of the invention. The claims will serve to define the invention.

EXAMPLES

Examples were simulated using the process simulator Aspen Plus™ from Aspen Technology Inc. A summary table of Examples and results is provided in Table 10 and FIGS. 9 and 10.

The following specific process features and parameters were common to all simulations: (1) the mixed process feed to the RWGS reactor system consisted of 1500 lbmol/hr $CO_2$ and 4500 lbmol/hr $H_2$ in the $H_2/CO$ ratio 3:1, at 100° F., and at pressure so as to produce product syngas at 415 psia (accounting for different pressure drop through different examples); (2) $CO_2$, for example, may have been captured from an industrial point source emission, captured directly from ambient air (e.g. using Direct Air Capture or "DAC" technology, sourced via pipeline, truck, rail, ship or other means; (3) $H_2$, for example, may have been produced via water electrolysis, steam-methane reforming, partial oxidation, pyrolysis, refinery operations, sourced via pipeline, truck, rail, ship, or other means (4) the product syngas is produced at 415 psia and 100° F. (after cooling); (5) heat is provided, in these examples, to the process (e.g., to preheat feeds and provide heat to drive the endothermic RWGS reaction) by the combustion of natural gas with ambient air; (6) said natural gas has the following composition: 94.0% methane, 3.5% ethane, 1.5% propane, 0.5% nitrogen, and 0.5% carbon dioxide (compositions in mole %); (7) alternate means of providing heat (not simulated) are possible, and may include, for example, electric heating, hydrogen fuel, coal, oil, hydrocarbon fuels, other fuels, oxycombustion; (7) $CO_2$ capture may optionally be included from the combustion flue gas, and the captured $CO_2$ may optionally be used as feed to the RWGS reactor(s); (8) RWGS reactors are designed and operated such that the RWGS reaction closely approaches equilibrium at the exit of all RWGS reactors.

Example 1: Single-Stage RWGS Reaction at 1742° F. (950° C.)

Figure 3:
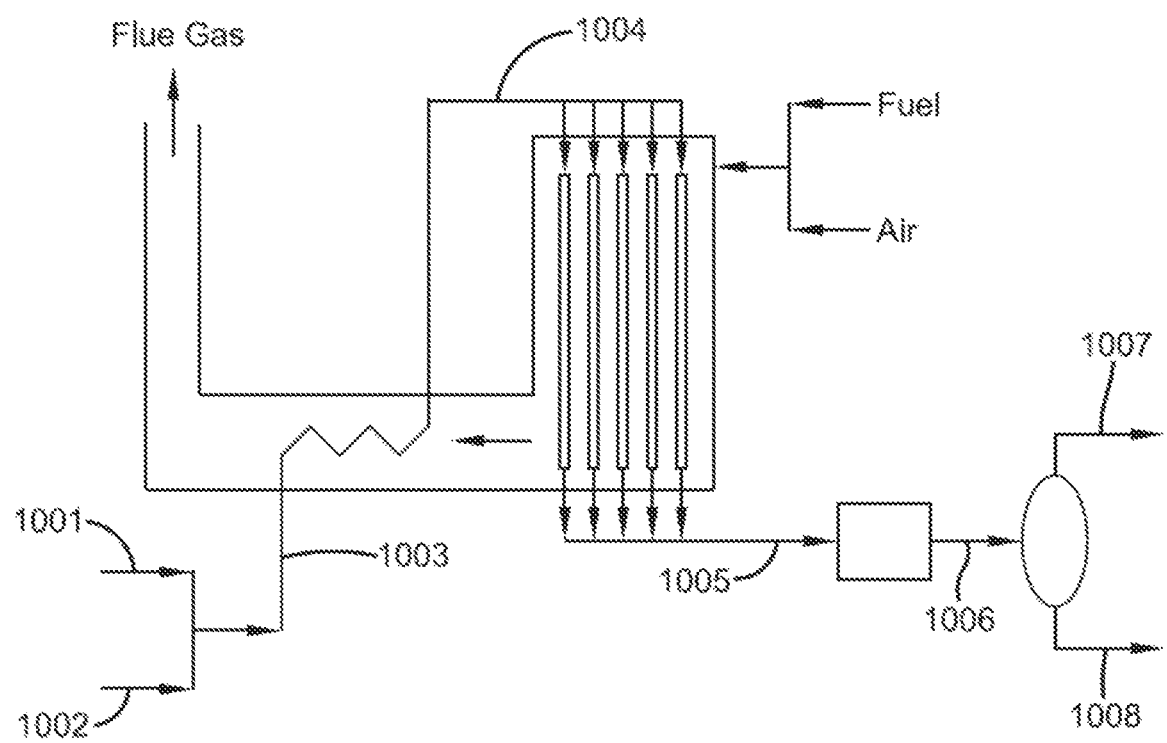
FIG. 3 is a schematic diagram of an example process with a single-stage RWGS reaction according to Example 1 described herein.

The single-stage RWGS process of this example is shown in FIG. 3. The mixed $H_2+CO_2$ feed is preheated to 1000° F. (538° C.), and provided to a fired tubular RWGS reactor (similar in design to a steam-methane reformer for the production of hydrogen from steam and methane, for which designs are well-known). The RWGS reactor is operated at high outlet temperature 1742° F. (950° C.), representative of an operating temperature for expensive high-nickel alloy tubes in a fired tubular RWGS reactor. $CO_2$ conversion via RWGS is 80%. The product syngas contains 94% $H_2+CO$ on a dry basis and with $H_2:CO$ ratio of 2.75:1. The firing of 291 lbmol/hr natural gas fuel results in 310 lbmol/hr of $CO_2$ contained in the flue gas. Additional heat and material balance data is provided in Table 1.

TABLE 1

| Stream | | CO2 Feed | H2 Feed | Mixed Feed | RWGS Feed | RWGS Effluent | Cooled Syngas | Product Syngas | Water |
|---|---|---|---|---|---|---|---|---|---|
| Stream No. | | 1001 | 1002 | 1003 | 1004 | 1005 | 1006 | 1007 | 1008 |
| Temperature | F. | 100 | 100 | 87 | 1000 | 1742 | 100 | 100 | 100 |
| Pressure | psia | 495 | 495 | 480 | 460 | 440 | 415 | 415 | 415 |
| Total Flow | lbmol/hr | 1500.0 | 4500.0 | 6000.0 | 6000.0 | 6000.0 | 6000.0 | 4811.6 | 1188.4 |
| CO | lbmol/hr | 0.0 | 0.0 | 0.0 | 0.0 | 1198.8 | 1198.8 | 1198.8 | 0.0 |
| H2 | lbmol/hr | 0.0 | 4500.0 | 4500.0 | 4500.0 | 3301.2 | 3301.2 | 3301.2 | 0.0 |
| CO2 | lbmol/hr | 1500.0 | 0.0 | 1500.0 | 1500.0 | 301.2 | 301.2 | 301.2 | 0.0 |
| H2O | lbmol/hr | 0.0 | 0.0 | 0.0 | 0.0 | 1198.8 | 1198.8 | 10.4 | 1188.3 |

Example 2: Single-Stage RWGS at 1000° F. (538° C.)

Figure 4:
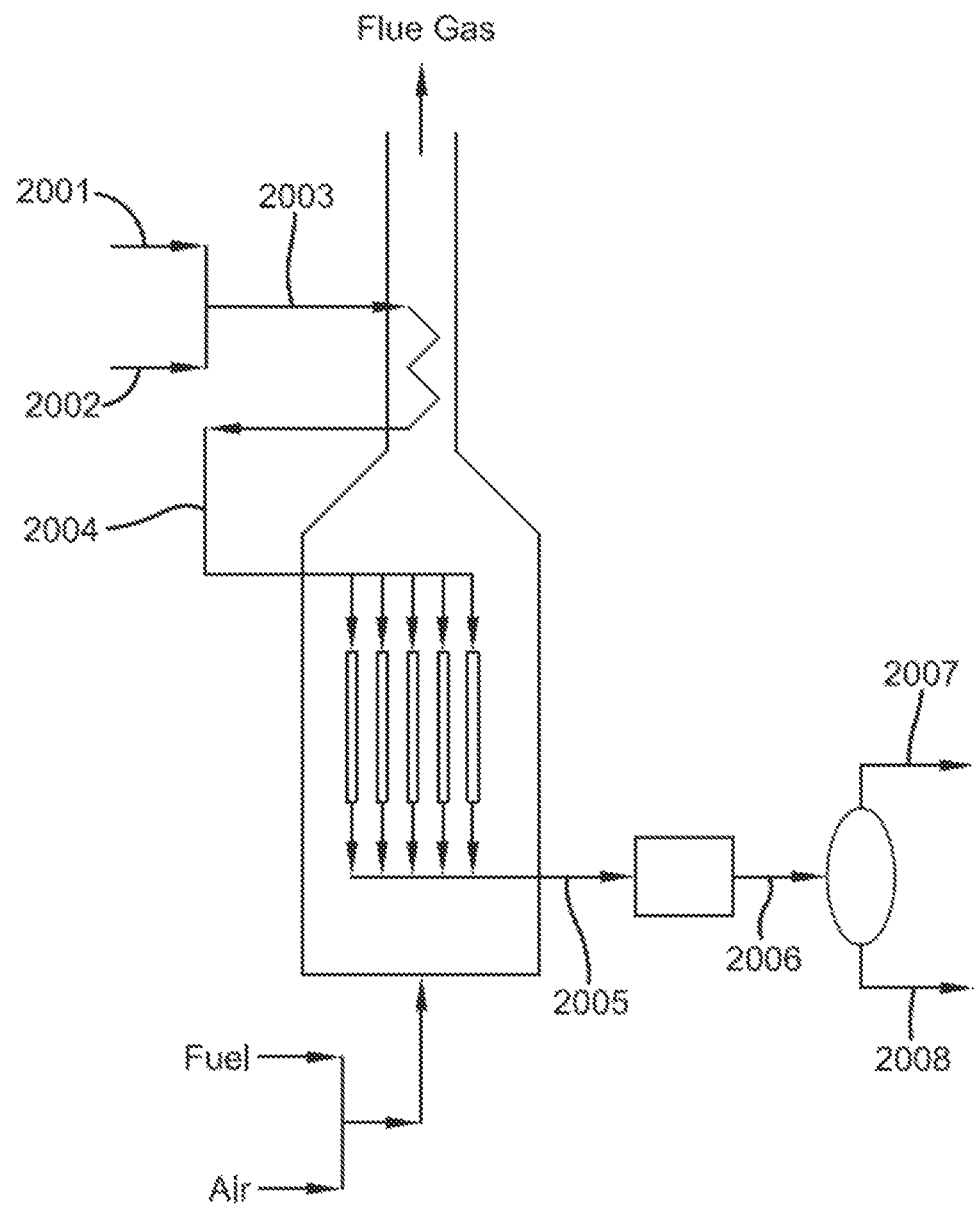
FIG. 4 is a schematic diagram of an example process with a single-stage RWGS reaction according to Example 2 described herein.

The single-stage RWGS process of this example is shown in FIG. 4. The mixed $H_2+CO_2$ feed is preheated to 1000° F. (538° C.) and provided to a fired heater-style RWGS reactor (similar in design to a typical refinery fired heater, for which designs are well-known). The RWGS reactor is operated at low outlet temperature 1000° F. (538° C.), representative of an operating temperature for low cost stainless steel tubes in a fired heater-style RWGS reactor; alternate low temperature RWGS process configurations (not shown) may include waste heat recovery (e.g. without dedicated firing) and/or adiabatic reactors (e.g. packed bed). $CO_2$ conversion via this single-stage RWGS is 54%. The product syngas contains 87% $H_2+CO$ on a dry basis and with $H_2:CO$ ratio of 4.58:1. The firing of 166 lbmol/hr natural gas fuel results in 177 lbmol/hr of $CO_2$ contained in the flue gas. Additional heat and material balance data is provided in Table 2.

TABLE 2

| Stream | | CO2 Feed | H2 Feed | Mixed Feed | RWGS Feed | RWGS Effluent | Cooled Syngas | Product Syngas | Water |
|---|---|---|---|---|---|---|---|---|---|
| Stream No. | | 2001 | 2002 | 2003 | 2004 | 2005 | 2006 | 2007 | 2008 |
| Temperature | F. | 100 | 100 | 87 | 1000 | 1000 | 100 | 100 | 100 |
| Pressure | psia | 495 | 495 | 480 | 460 | 440 | 415 | 415 | 415 |
| Total Flow | lbmol/hr | 1500.0 | 4500.0 | 6000.0 | 6000.0 | 6000.0 | 6000.0 | 5205.2 | 794.8 |
| CO | lbmol/hr | 0.0 | 0.0 | 0.0 | 0.0 | 806.1 | 806.1 | 806.1 | 0.0 |
| H2 | lbmol/hr | 0.0 | 4500.0 | 4500.0 | 4500.0 | 3693.9 | 3693.9 | 3693.9 | 0.0 |
| CO2 | lbmol/hr | 1500.0 | 0.0 | 1500.0 | 1500.0 | 693.9 | 693.9 | 693.9 | 0.0 |
| H2O | lbmol/hr | 0.0 | 0.0 | 0.0 | 0.0 | 806.1 | 806.1 | 11.4 | 794.7 |

The data from Examples 1 and 2 show that $CO_2$ conversion via the RWGS reaction through a single-stage RWGS process for a given feed (in this case 1500 lbmol/hr $CO_2$ and 4500 lbmol/hr $H_2$) under similar operating conditions is a strong function of RWGS reactor outlet temperature, as illustrated by comparison of Example 1 at 1742° F. showing 80% $CO_2$ conversion versus Example 2 at 1000° F. showing 54% $CO_2$ conversion.

Figure 5:
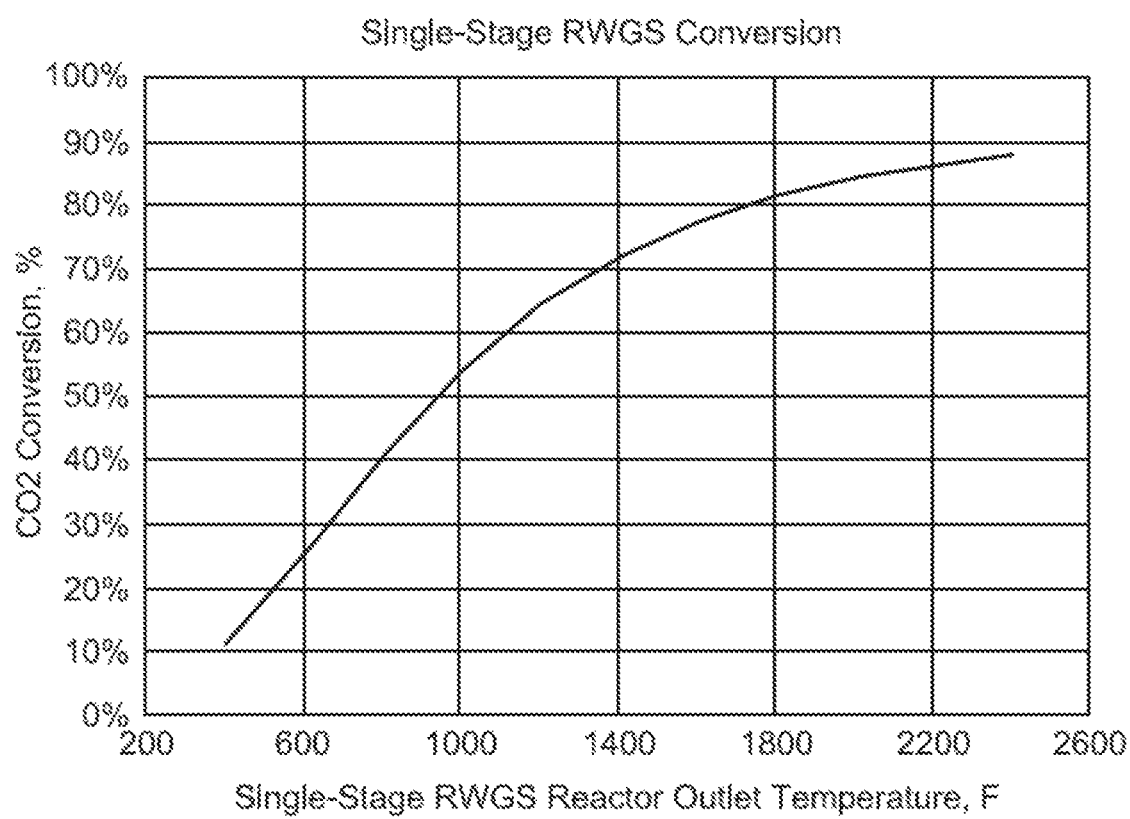
FIG. 5 is a graphical plot of single-stage RWGS reactions relative to temperature.

Additional simulation results of single-stage RWGS processes operated at RWGS reactor outlet temperatures over the range 400° F. to 2400° F. are shown in Table 3 and FIG. 5.

TABLE 3

| RWGS Outlet Temperature ° F. | RWGS Outlet Temperature ° C. | $CO_2$ Conversion % |
|---|---|---|
| 400 | 204.4 | 11% |
| 600 | 315.6 | 25% |
| 800 | 426.7 | 40% |
| 1000 | 537.8 | 54% |
| 1200 | 648.9 | 64% |
| 1400 | 760.0 | 72% |
| 1600 | 871.1 | 77% |
| 1800 | 982.2 | 81% |
| 2000 | 1093.3 | 84% |
| 2200 | 1204.4 | 86% |
| 2400 | 1315.6 | 88% |

Figure 6:
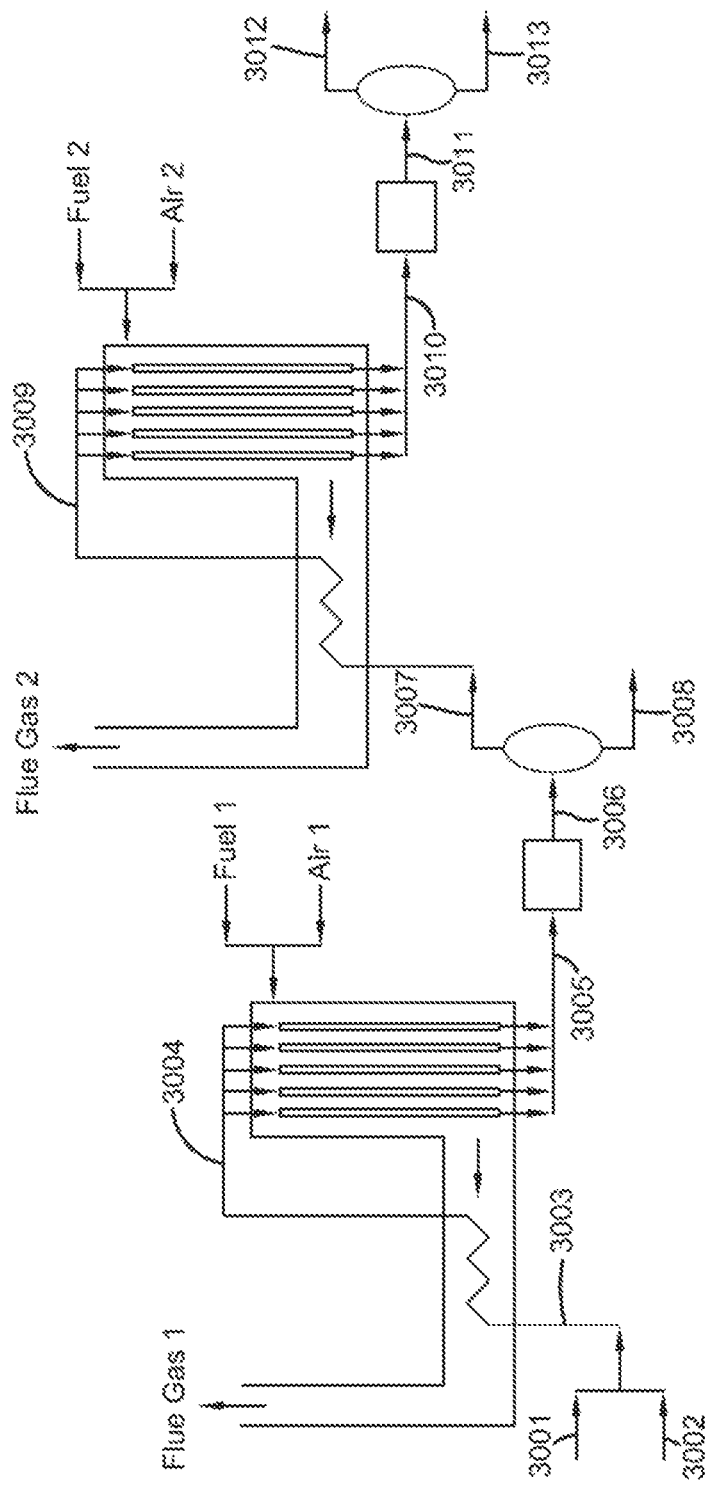
FIG. 6 is a schematic diagram of an example process with a two-stage RWGS reaction according to Example 3 described herein.

Example 3: Two-Stage RWGS at 1742° F. & 1742° F. With Water Knockout Via Cooling & Condensation The two-stage RWGS process of this example is shown in FIG. 6. The mixed $H_2+CO_2$ feed is preheated to 1000° F. and provided to a first stage fired tubular RWGS reactor, where the RWGS reactor is operated at high outlet temperature 1742° F. (950° C.). The syngas is cooled to 100° F., and much of the water formed by the RWGS reaction in the first RWGS reactor stage (which is present in the syngas effluent the first RWGS reactor stage) is condensed and removed (99.2% removal). The syngas is reheated again to 1000° F. and provided to a second stage fired tubular RWGS reactor, where the RWGS reactor is again operated at high outlet temperature 1742° F. (950° C.). Overall $CO_2$ conversion via RWGS at the effluent of the first and second stage RWGS reactors are 80% and 95% (respectively). The product syngas contains 98% $H_2+CO$ on a dry basis and with $H_2:CO$ ratio of 2.16:1.

The two-stage RWGS product syngas of Example 3 is improved relative to the single-stage RWGS product syngas of Examples 1 and 2, having greater $CO_2$ conversion, greater $H_2+CO$ content (target synthesis reactants), and $H_2:CO$ ratio near 2 (a typical target $H_2:CO$ ratio for Fischer-Tropsch synthesis, methanol synthesis, and other synthesis reactions). The firing of 291 lbmol/hr natural gas fuel in the first stage results in 310 lbmol/hr of $CO_2$ contained in the flue gas from the first stage. The firing of 183 lbmol/hr natural gas fuel in the second stage results in 195 lbmol/hr of $CO_2$ contained in the flue gas from the second stage. Additional heat and material balance data is provided in Table 4.

Further practical value of the two (or multi) stage RWGS reactor process is recognized when the two stages are designed differently (including metallurgy and/or materials of construction) or operated at different operating conditions. A wide range of different designs and operating conditions are possible. Different designs of the stages (including and/or materials of construction), operation of the stages at different RWGS reactor outlet temperatures, with water removal, with heat integration, and/or combinations are of particular interest as will be shown in additional Examples to follow.

TABLE 4

| Stream | | CO2 Feed | H2 Feed | Mixed Feed | RWGS 1 Feed | RWGS 1 Effluent | Cooled Syngas 1 | Product Syngas 1 |
|---|---|---|---|---|---|---|---|---|
| Stream No. | | 3001 | 3002 | 3003 | 3004 | 3005 | 3006 | 3007 |
| Temperature | F. | 100 | 100 | 84 | 1000 | 1742 | 100 | 100 |
| Pressure | psia | 560 | 560 | 545 | 525 | 505 | 480 | 480 |
| Total Flow | lbmol/hr | 1500.0 | 4500.0 | 6000.0 | 6000.0 | 6000.0 | 6000.0 | 4810.3 |
| CO | lbmol/hr | 0.0 | 0.0 | 0.0 | 0.0 | 1198.8 | 1198.8 | 1198.8 |
| H2 | lbmol/hr | 0.0 | 4500.0 | 4500.0 | 4500.0 | 3301.2 | 3301.2 | 3301.2 |
| CO2 | lbmol/hr | 1500.0 | 0.0 | 1500.0 | 1500.0 | 301.2 | 301.2 | 301.2 |
| H2O | lbmol/hr | 0.0 | 0.0 | 0.0 | 0.0 | 1198.8 | 1198.8 | 9.2 |

| Stream | | Water 1 | RWGS 2 Feed | RWGS 2 Effluent | Cooled Syngas 2 | Product Syngas 2 | Water 2 |
|---|---|---|---|---|---|---|---|
| Stream No. | | 3008 | 3009 | 3010 | 3011 | 3012 | 3013 |
| Temperature | F. | 100 | 1000 | 1742 | 100 | 100 | 100 |
| Pressure | psia | 480 | 460 | 440 | 415 | 415 | 415 |

TABLE 4-continued

| | | | | | | | |
|---|---|---|---|---|---|---|---|
| Total Flow | lbmol/hr | 1189.7 | 4810.3 | 4810.3 | 4810.3 | 4585.3 | 225.0 |
| CO | lbmol/hr | 0.0 | 1198.8 | 1424.5 | 1424.5 | 1424.5 | 0.0 |
| H2 | lbmol/hr | 0.0 | 3301.2 | 3075.5 | 3075.5 | 3075.5 | 0.0 |
| CO2 | lbmol/hr | 0.0 | 301.2 | 75.5 | 75.5 | 75.5 | 0.0 |
| H2O | lbmol/hr | 1189.6 | 9.2 | 234.9 | 234.9 | 9.9 | 225.0 |

Figure 7:
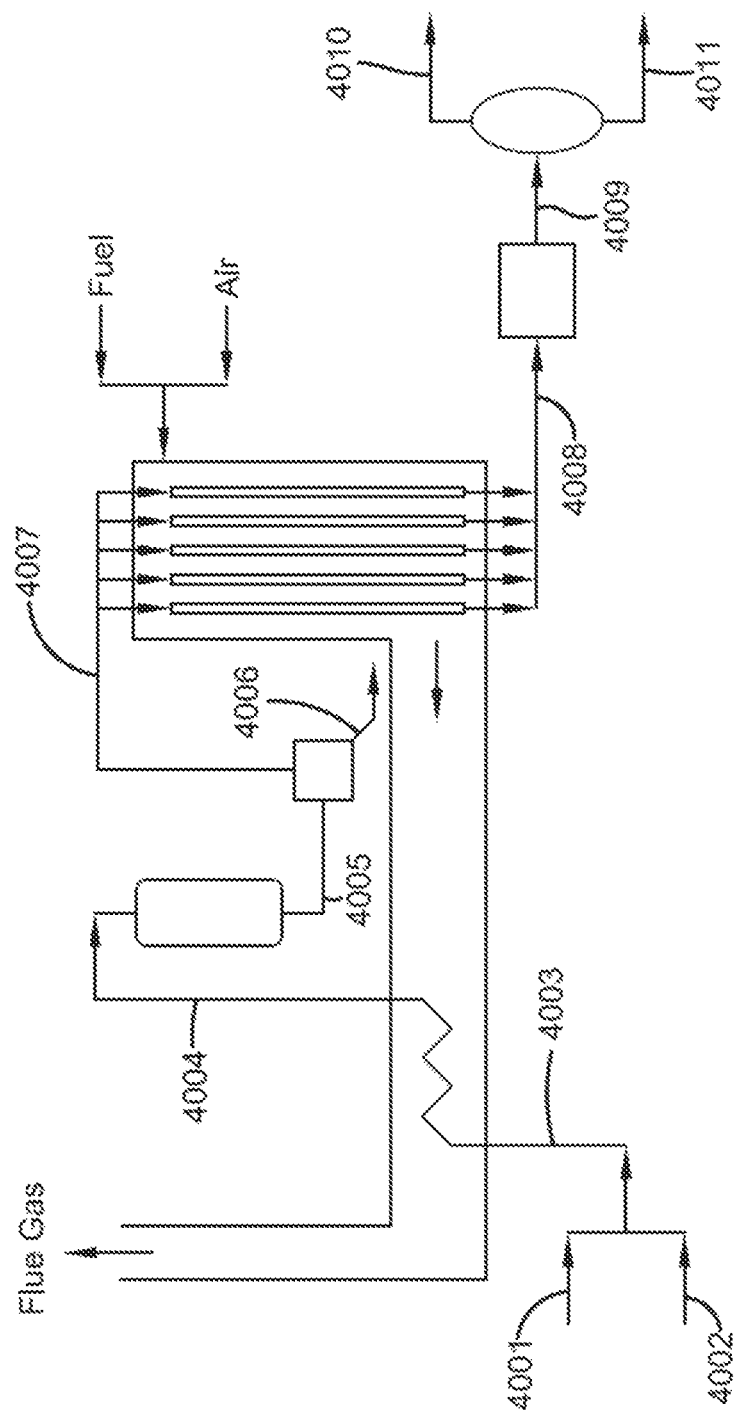
FIG. 7 is a schematic diagram of an example process with a two-stage RWGS reaction according to Examples 4, 5 and 6 described herein.

Example 4: Two-Stage RWGS at 1000° F. & 1742° F., With Heat Integration and No Inter-Stage Water Removal The two-stage RWGS process of this example is shown in FIG. 7. The mixed $H_2+CO_2$ feed is preheated to 1249° F. and provided to an adiabatic RWGS reactor (e.g. packed catalyst bed). Sufficient RWGS catalyst is provided to closely approach equilibrium of the RWGS reaction, and the reacted gas exits the first stage RWGS reactor at 1000° F. An alternate design (not shown) may have used a convectively heated RWGS reactor to achieve similar (or improved) $CO_2$ conversion. The first stage RWGS reactor effluent gas is provided to a second stage fired tubular RWGS reactor. The second stage RWGS reactor is operated at high outlet temperature 1742° F. (950° C.). Without inter-stage water removal, the overall $CO_2$ conversion results are similar to series combination of Examples 2 and 1, at 54% and 80% respectively. Similar to Example 1, the firing of 291 lbmol/hr natural gas fuel results in 310 lbmol/hr of $CO_2$ contained in the flue gas. Additional heat and material balance data is provided in Table 5.

While $CO_2$ conversion of this Example 5 is similar to that of Example 1, appreciable benefits of this Example 5 (relative to Example 1) are in lower cost equipment design and metallurgy (or materials of construction) of the first RWGS stage associated with its low temperature operation and packed bed reactor design. Less conversion occurs in the second stage, and the size of the costly fired tubular RWGS reactor with expensive high-nickel alloy tubes is significantly reduced (relative to Example 1).

TABLE 5

| Stream | | CO2 Feed | H2 Feed | Mixed Feed | RWGS 1 Feed | RWGS 1 Effluent | Water 1 | RWGS 2 Feed | RWGS 2 Effluent | Cooled Syngas 2 | Product Syngas 2 | Water 2 |
|---|---|---|---|---|---|---|---|---|---|---|---|---|
| Stream No. | | 4001 | 4002 | 4003 | 4004 | 4005 | 4006 | 4007 | 4008 | 4009 | 4010 | 4011 |
| Temperature | F. | 100 | 100 | 86 | 1249 | 1000 | 1000 | 1000 | 1742 | 100 | 100 | 100 |
| Pressure | psia | 520 | 520 | 505 | 485 | 465 | 465 | 460 | 440 | 415 | 415 | 415 |
| Total Flow | lbmol/hr | 1500.0 | 4500.0 | 6000.0 | 6000.0 | 6000.0 | 0.0 | 6000.0 | 6000.0 | 6000.0 | 4811.6 | 1188.4 |
| CO | lbmol/hr | 0.0 | 0.0 | 0.0 | 0.0 | 806.2 | 0.0 | 806.2 | 1198.8 | 1198.8 | 1198.8 | 0.0 |
| H2 | lbmol/hr | 0.0 | 4500.0 | 4500.0 | 4500.0 | 3693.8 | 0.0 | 3693.8 | 3301.2 | 3301.2 | 3301.2 | 0.0 |
| CO2 | lbmol/hr | 1500.0 | 0.0 | 1500.0 | 1500.0 | 693.8 | 0.0 | 693.8 | 301.2 | 301.2 | 301.2 | 0.0 |
| H2O | lbmol/hr | 0.0 | 0.0 | 0.0 | 0.0 | 806.2 | 0.0 | 806.2 | 1198.8 | 1198.8 | 10.4 | 1188.3 |

Example 5: Two-Stage RWGS at 1000° F. & 1742° F., With Heat Integration & 50% Inter-Stage Water Removal Using High Temperature Membrane The two-stage RWGS process of this example is shown in FIG. 7. This Example 5 is similar to previous Example 4, except that 50% of the water formed by the RWGS reaction in the first RWGS reactor stage (which is present in the syngas effluent the first RWGS reactor stage) is removed using a high temperature membrane system. Overall CO2 conversion via RWGS at the effluent of the first and second stage RWGS reactors are 54% and 84% (respectively). The product syngas contains 95% $H_2$+CO on a dry basis and with $H_2$:CO ratio of 2.55:1. The firing of 285 lbmol/hr natural gas fuel results in 304 lbmol/hr of CO2 contained in the flue gas. Additional heat and material balance data is provided in Table 6.

The benefits of lower cost equipment design (discussed above in Example 4) also apply to this Example 5. Also relative to Example 4, $CO_2$ conversion is increased from 80% to 84%; and beneficial reductions are recognized in heat transfer duty (resulting in smaller equipment), fuel firing, and $CO_2$ contained in the flue gas. Relative to the single-stage RGWS designs of Examples 1 and 2, both cost and performance are improved.

TABLE 6

| Stream | | CO2 Feed | H2 Feed | Mixed Feed | RWGS 1 Feed | RWGS 1 Effluent | Water 1 | RWGS 2 Feed | RWGS 2 Effluent | Cooled Syngas 2 | Product Syngas 2 | Water 2 |
|---|---|---|---|---|---|---|---|---|---|---|---|---|
| Stream No. | | 4001 | 4002 | 4003 | 4004 | 4005 | 4006 | 4007 | 4008 | 4009 | 4010 | 4011 |
| Temperature | F. | 100 | 100 | 86 | 1249 | 1000 | 1000 | 1000 | 1742 | 100 | 100 | 100 |
| Pressure | psia | 520 | 520 | 505 | 485 | 465 | 465 | 460 | 440 | 415 | 415 | 415 |
| Total Flow | lbmol/hr | 1500.0 | 4500.0 | 6000.0 | 6000.0 | 6000.0 | 403.1 | 5596.9 | 5596.9 | 5596.9 | 4744.2 | 852.7 |
| CO | lbmol/hr | 0.0 | 0.0 | 0.0 | 0.0 | 806.2 | 0.0 | 806.2 | 1266.1 | 1266.1 | 1266.1 | 0.0 |
| H2 | lbmol/hr | 0.0 | 4500.0 | 4500.0 | 4500.0 | 3693.8 | 0.0 | 3693.8 | 3233.9 | 3233.9 | 3233.9 | 0.0 |
| CO2 | lbmol/hr | 1500.0 | 0.0 | 1500.0 | 1500.0 | 693.8 | 0.0 | 693.8 | 233.9 | 233.9 | 233.9 | 0.0 |
| H2O | lbmol/hr | 0.0 | 0.0 | 0.0 | 0.0 | 806.2 | 403.1 | 403.1 | 863.0 | 863.0 | 10.3 | 852.7 |

Example 6: Two-Stage RWGS at 1000° F. & 1742° F., With Heat Integrated & 90% Inter-Stage Water Removal Using High Temperature Adsorbent The two-stage RWGS process of this example is shown in FIG. 7. This Example 6 is similar to previous Example 5, except that 90% of the water formed by the RWGS reaction in the first RWGS reactor stage (which is present in the syngas effluent the first RWGS reactor stage) is removed using a high temperature adsorbent system. Overall CO2 conversion via RWGS at the effluent of the first and second stage RWGS reactors are 54% and 88% (respectively). The product syngas contains 96% $H_2$+CO on a dry basis and with $H_2$:CO ratio of 2.39:1. The firing of 280 lbmol/hr natural gas fuel results in 299 lbmol/hr of $CO_2$ contained in the flue gas. Additional heat and material balance data is provided in Table 7.

The benefits of lower cost equipment design (discussed above in Example 4) also apply to this Example 6. Relative to Example 5, $CO_2$ conversion is increased from 84% to 88%; and beneficial reductions are recognized in heat transfer duty (resulting in smaller equipment), fuel firing, and $CO_2$ contained in the flue gas. Relative to the single-stage RGWS designs of Examples 1 and 2, both cost and performance are improved.

TABLE 7

| Stream | | CO2 Feed | H2 Feed | Mixed Feed | RWGS 1 Feed | RWGS 1 Effluent | Water 1 | RWGS 2 Feed |
|---|---|---|---|---|---|---|---|---|
| Stream No. | | 4001 | 4002 | 4003 | 4004 | 4005 | 4006 | 4007 |
| Temperature | F. | 100 | 100 | 86 | 1249 | 1000 | 1000 | 1000 |
| Pressure | psia | 520 | 520 | 505 | 485 | 465 | 465 | 460 |
| Total Flow | lbmol/hr | 1500.0 | 4500.0 | 6000.0 | 6000.0 | 6000.0 | 725.6 | 5274.4 |
| CO | lbmol/hr | 0.0 | 0.0 | 0.0 | 0.0 | 806.2 | 0.0 | 806.2 |
| H2 | lbmol/hr | 0.0 | 4500.0 | 4500.0 | 4500.0 | 3693.8 | 0.0 | 3693.8 |
| CO2 | lbmol/hr | 1500.0 | 0.0 | 1500.0 | 1500.0 | 693.8 | 0.0 | 693.8 |
| H2O | lbmol/hr | 0.0 | 0.0 | 0.0 | 0.0 | 806.2 | 725.6 | 80.6 |

| Stream | | RWGS 2 Effluent | Cooled Syngas 2 | Product Syngas 2 | Water 2 |
|---|---|---|---|---|---|
| Stream No. | | 4008 | 4009 | 4010 | 4011 |
| Temperature | F. | 1742 | 100 | 100 | 100 |
| Pressure | psia | 440 | 415 | 415 | 415 |
| Total Flow | lbmol/hr | 5274.4 | 5274.4 | 4683.9881 | 590.4564 |
| CO | lbmol/hr | 1326.1 | 1326.1 | 1326.124 | 0.000591 |
| H2 | lbmol/hr | 3173.9 | 3173.9 | 3173.8726 | 0.002801 |
| CO2 | lbmol/hr | 173.9 | 173.9 | 173.86672 | 0.008702 |
| H2O | lbmol/hr | 600.6 | 600.6 | 10.124805 | 590.443 |

Figure 8:
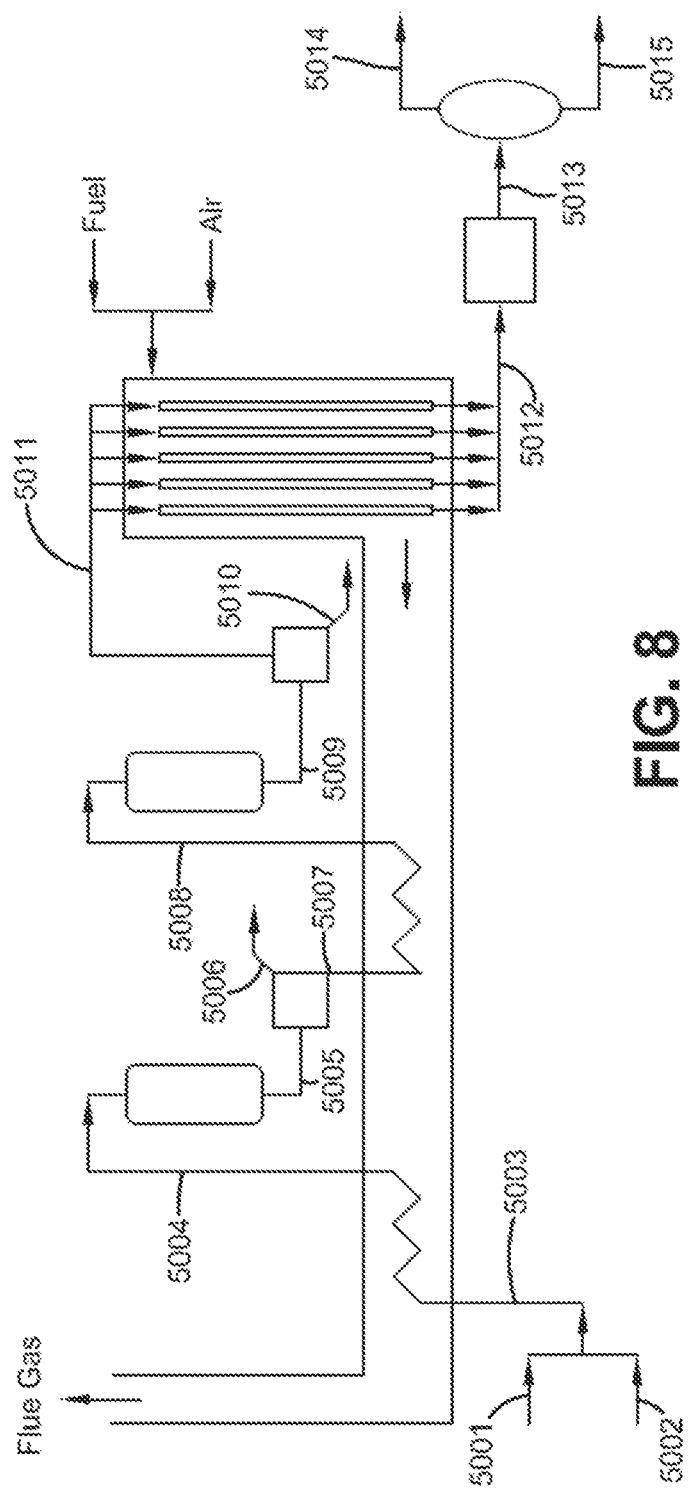
FIG. 8 is a schematic diagram of an example process with a three-stage RWGS reaction according to Example 7 and 8 described herein.

Example 7: Three-Stage RWGS at 1000° F., 1000° F., & 1742° F., With Heat Integration & 50% Inter-stage Water Removal Using High Temperature Adsorbents The three-stage RWGS process of this example is shown in FIG. 8. The mixed $H_2+CO_2$ feed is preheated to 1249° F. and provided to an adiabatic RWGS reactor (e.g. packed catalyst bed). Sufficient RWGS catalyst is provided to closely approach equilibrium of the RWGS reaction, and the reacted gas exits the first stage RWGS reactor at 1000° F. 50% of the water formed by the RWGS reaction in the first RWGS reactor stage (which is present in the syngas effluent the first RWGS reactor stage) is removed using a high temperature adsorbent system. The water-lean first stage RWGS reactor effluent gas is reheated to 1047° F. and provided to a second stage adiabatic RWGS reactor; again, sufficient RWGS catalyst is provided to closely approach equilibrium of the RWGS reaction, and the reacted gas exits the second stage RWGS reactor at 1000° F. 50% of the water which is present in the syngas effluent the second RWGS reactor stage is removed using a high temperature adsorbent system. The water-lean second stage RWGS reactor effluent gas is provided to a third stage fired tubular RWGS reactor.

The third stage RWGS reactor is operated at high outlet temperature 1742° F. (950° C.). Overall $CO_2$ conversion via RWGS at the effluent of the first, second, and third stage RWGS reactors are 54%, 63%, and 88% (respectively). The product syngas contains 96% $H_2$+CO on a dry basis and with $H_2$:CO ratio of 2.42:1. The firing of 281 lbmol/hr natural gas fuel results in 300 lbmol/hr of $CO_2$ contained in the flue gas. Additional heat and material balance data is provided in Table 8.

The benefits of lower cost equipment design (discussed above in Example 4) also apply to this Example 7. Relative to the two-stage Example 5, $CO_2$ conversion is increased from 84% to 88%; and beneficial reductions are recognized in heat transfer duty (resulting in smaller equipment), fuel firing, and $CO_2$ contained in the flue gas. Relative to the single-stage RGWS designs of Examples 1 and 2, both cost and performance are improved.

Additional stages (e.g. 4, 5, 100+) are possible. Benefits of highly integrated multi-stage systems, while applicable to large-scale systems, are particularly advantageous in small-scale systems where efficient and/or advanced manufacturing and assembly techniques (e.g. 3D printing, etching, repetitive parts, shop manufacturing) may be used, for example to minimize manufacturing costs.

TABLE 8

| Stream | | CO2 Feed | H2 Feed | Mixed Feed | RWGS 1 Feed | RWGS 1 Effluent | Water 1 | R1 to R2 Syngas | RWGS 2 Feed |
|---|---|---|---|---|---|---|---|---|---|
| Stream No. | | 5001 | 5002 | 5003 | 5004 | 5005 | 5006 | 5007 | 5008 |
| Temperature | F. | 100 | 100 | 84 | 1249 | 1000 | 1000 | 1000 | 1047 |
| Pressure | psia | 565 | 565 | 550 | 530 | 510 | 510 | 505 | 485 |
| Total Flow | lbmol/hr | 1500.0 | 4500.0 | 6000.0 | 6000.0 | 6000.0 | 403.2 | 5596.8 | 5596.8 |
| CO | lbmol/hr | 0.0 | 0.0 | 0.0 | 0.0 | 806.3 | 0.0 | 806.3 | 806.3 |
| H2 | lbmol/hr | 0.0 | 4500.0 | 4500.0 | 4500.0 | 3693.7 | 0.0 | 3693.7 | 3693.7 |
| CO2 | lbmol/hr | 1500.0 | 0.0 | 1500.0 | 1500.0 | 693.7 | 0.0 | 693.7 | 693.7 |
| H2O | lbmol/hr | 0.0 | 0.0 | 0.0 | 0.0 | 806.3 | 403.2 | 403.2 | 403.2 |

TABLE 8-continued

| Stream | | RWGS 2 Effluent | Water 2 | RWGS 3 Feed | RWGS 3 Effluent | Cooled Syngas | Product Syngas | Water 3 |
|---|---|---|---|---|---|---|---|---|
| Stream No. | | 5009 | 5010 | 5011 | 5012 | 5013 | 5014 | 5015 |
| Temperature | F. | 1000 | 1000 | 1000 | 1742 | 100 | 100 | 100 |
| Pressure | psia | 465 | 465 | 460 | 440 | 415 | 415 | 415 |
| Total Flow | lbmol/hr | 5596.8 | 268.4 | 5328.4 | 5328.4 | 5328.4 | 4694.5 | 633.9 |
| CO | lbmol/hr | 939.9 | 0.0 | 939.9 | 1315.6 | 1315.6 | 1315.6 | 0.0 |
| H2 | lbmol/hr | 3560.1 | 0.0 | 3560.1 | 3184.4 | 3184.4 | 3184.4 | 0.0 |
| CO2 | lbmol/hr | 560.1 | 0.0 | 560.1 | 184.4 | 184.4 | 184.4 | 0.0 |
| H2O | lbmol/hr | 536.8 | 268.4 | 268.4 | 644.1 | 644.1 | 10.2 | 633.9 |

Example 8: Three-Stage RWGS at 1000° F., 1000° F., & 1742° F., With Heat Integration & 90% Inter-stage Water Removal Using High Temperature Membranes The three-stage RWGS process of this example is shown in FIG. 8. This Example 8 is similar to previous Example 7, except that 90% of the water (formed by the RWGS reactions) present in the syngas effluent the first and second RWGS reactor stages is removed using high temperature membrane systems. Overall $CO_2$ conversions at the effluent of the first, second, and third stage RWGS reactors are 54%, 71%, and 93% (respectively). The product syngas contains 98% $H_2$+CO on a dry basis and with $H_2$:CO ratio of 2.24:1. The firing of 277 lbmol/hr natural gas fuel results in 295 lbmol/hr of $CO_2$ contained in the flue gas. Additional heat and material balance data is provided in Table 9.

The benefits of lower cost equipment design (discussed above in Example 4) also apply to this Example 8. Relative to the three-stage Example 7, $CO_2$ conversion is increased from 88% to 93%; and beneficial reductions are recognized in heat transfer duty (resulting in smaller equipment), fuel firing, and $CO_2$ contained in the flue gas. Relative to the two-stage Example 6, $CO_2$ conversion is increased from 88% to 93%; and beneficial reductions are recognized in heat transfer duty (resulting in smaller equipment), fuel firing, and $CO_2$ contained in the flue gas. Relative to the single-stage RGWS designs of Examples 1 and 2, both cost and performance are improved.

TABLE 9

| Stream | | CO2 Feed | H2 Feed | Mixed Feed | RWGS 1 Feed | RWGS 1 Effluent | Water 1 | R1 to R2 Syngas | RWGS 2 Feed |
|---|---|---|---|---|---|---|---|---|---|
| Stream No. | | 5001 | 5002 | 5003 | 5004 | 5005 | 5006 | 5007 | 5008 |
| Temperature | F. | 100 | 100 | 84 | 1249 | 1000 | 1000 | 1000 | 1100 |
| Pressure | psia | 565 | 565 | 550 | 530 | 510 | 510 | 505 | 485 |
| Total Flow | lbmol/hr | 1500.0 | 4500.0 | 6000.0 | 6000.0 | 6000.0 | 725.7 | 5274.3 | 5274.3 |
| CO | lbmol/hr | 0.0 | 0.0 | 0.0 | 0.0 | 806.3 | 0.0 | 806.3 | 806.3 |
| H2 | lbmol/hr | 0.0 | 4500.0 | 4500.0 | 4500.0 | 3693.7 | 0.0 | 3693.7 | 3693.7 |
| CO2 | lbmol/hr | 1500.0 | 0.0 | 1500.0 | 1500.0 | 693.7 | 0.0 | 693.7 | 693.7 |
| H2O | lbmol/hr | 0.0 | 0.0 | 0.0 | 0.0 | 806.3 | 725.7 | 80.6 | 80.6 |

| Stream | | RWGS 2 Effluent | Water 2 | RWGS 3 Feed | RWGS 3 Effluent | Cooled Syngas | Product Syngas 3 | Water 3 |
|---|---|---|---|---|---|---|---|---|
| Stream No. | | 5009 | 5010 | 5011 | 5012 | 5013 | 5014 | 5015 |
| Temperature | F. | 1000 | 1000 | 1000 | 1742 | 100 | 100 | 100 |
| Pressure | psia | 465 | 465 | 460 | 440 | 415 | 415 | 415 |
| Total Flow | lbmol/hr | 5274.3 | 311.4 | 4962.9 | 4962.9 | 4962.9 | 4619.5 | 343.4 |
| CO | lbmol/hr | 1071.7 | 0.0 | 1071.7 | 1390.4 | 1390.4 | 1390.4 | 0.0 |
| H2 | lbmol/hr | 3428.3 | 0.0 | 3428.3 | 3109.6 | 3109.6 | 3109.6 | 0.0 |
| CO2 | lbmol/hr | 428.3 | 0.0 | 428.3 | 109.6 | 109.6 | 109.5 | 0.0 |
| H2O | lbmol/hr | 346.0 | 311.4 | 34.6 | 353.3 | 353.3 | 10.0 | 343.4 |

Example 9: Three-Stage RWGS at 1000° F., 1000° F., & 1742° F., With Heat Integration & 90% Inter-stage Water Removal Using High Temperature Membranes & 90% CO2 Capture From Flue Gas, & H2 Feed Adjustment to Achieve Product Syngas H2/CO Ratio=2.0

Figure 9:
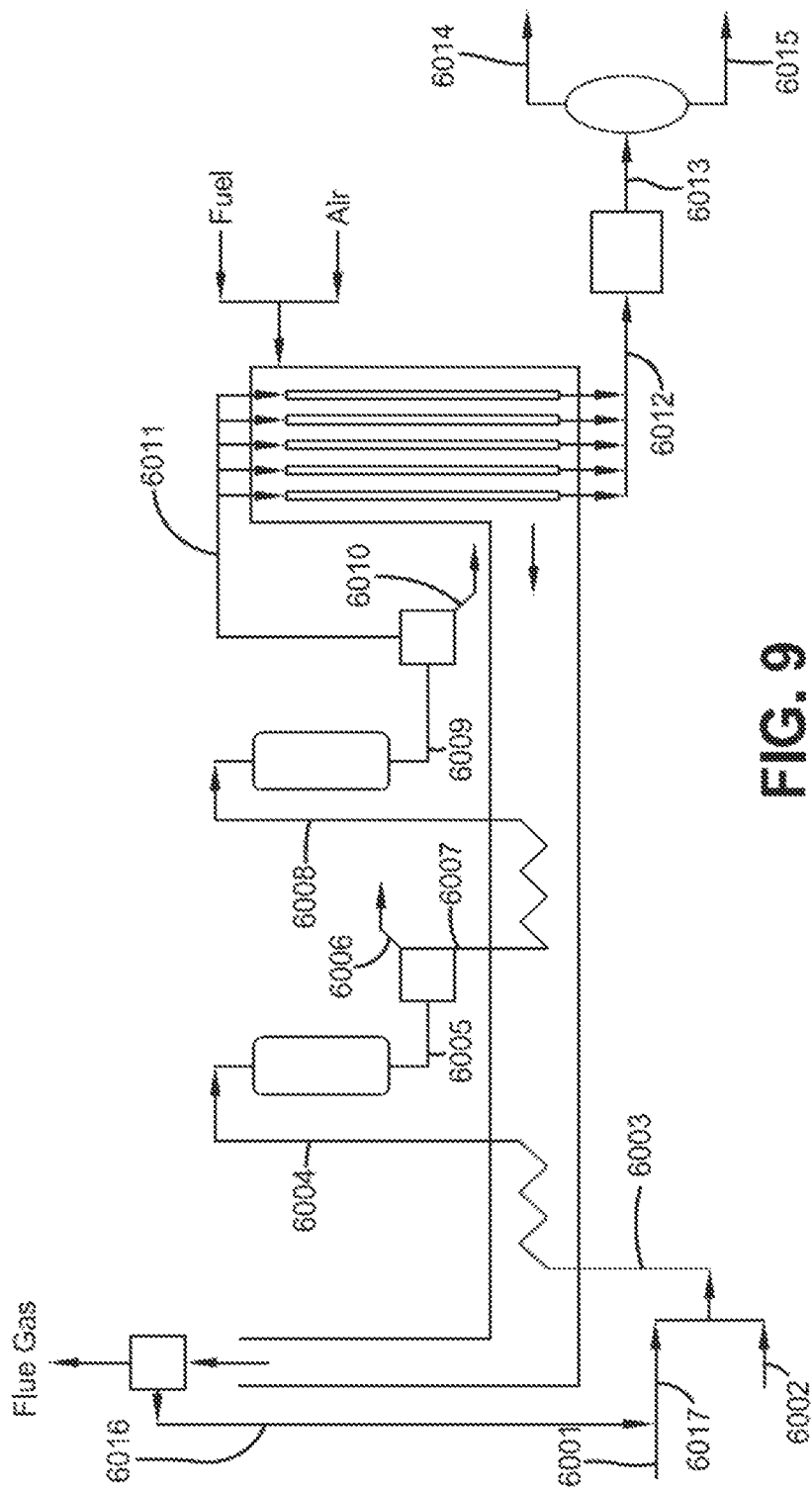
FIG. 9 is a schematic diagram of an example process with a three-stage RWGS reaction according to Example 9 described herein.

The three-stage RWGS process of this example is shown in FIG. 9. This Example 9 is similar to previous Example 8, except that a $CO_2$ capture system (e.g. an amine system or other $CO_2$ capture system) is added to the flue gas. 90% of the $CO_2$ contained in the flue gas is captured from the flue gas, compressed (not shown), and blended with the fresh $CO_2$ feed to the RWGS reactor system. The $H_2$ feed to the RWGS reactor system is adjusted to achieve a specified target $H_2$:CO ratio in the product syngas, which in this Example 9 is 2.0. Overall $CO_2$ conversions at the effluent of the first, second, and third stage RWGS reactors are 42%, 63%, and 90% (respectively). The product syngas contains 97% $H_2$+CO on a dry basis and with $H_2$:CO ratio of 2.00:1. The firing of 317 lbmol/hr natural gas fuel results in 338 lbmol/hr of $CO_2$ contained in the flue gas before the $CO_2$ capture system and 34 lbmol/hr of $CO_2$ contained in the flue gas after the $CO_2$ capture system. Additional Heat and Material Balance data is provided in Table 10.

Relative to Example 8, $CO_2$ contained in the flue gas after the $CO_2$ capture system is significantly reduced from 295 lbmol/hr to 34 lbmol/hr, contained CO+$H_2$ in the product syngas is increased by nominally 10% from 4500 lbmol/hr to 4955 lbmol/hr, and a target $H_2$:CO ratio of 2.0 is achieved in the product syngas. As exemplified by this example, adjustment of the $H_2$ feed flow, $CO_2$ feed flow, $CO_2$ capture and/or recycle flow, as well as other operating parameters in the RWGS reactor system (e.g. temperatures, pressures, water removal), can be used to control the production and qualities of product syngas, including the production rate of the product syngas, the $H_2$:CO ratio of the product syngas, and the molar percentage of $H_2$+CO in the product syngas. The recycle of a portion of the product syngas to the RWGS reactor system (e.g. to the feed or to an intermediate point in the RWGS process), removal and/or addition of components (e.g. from the product syngas), and/or other purification methods known in the art may also be used to impact the product syngas.

Figure 10:
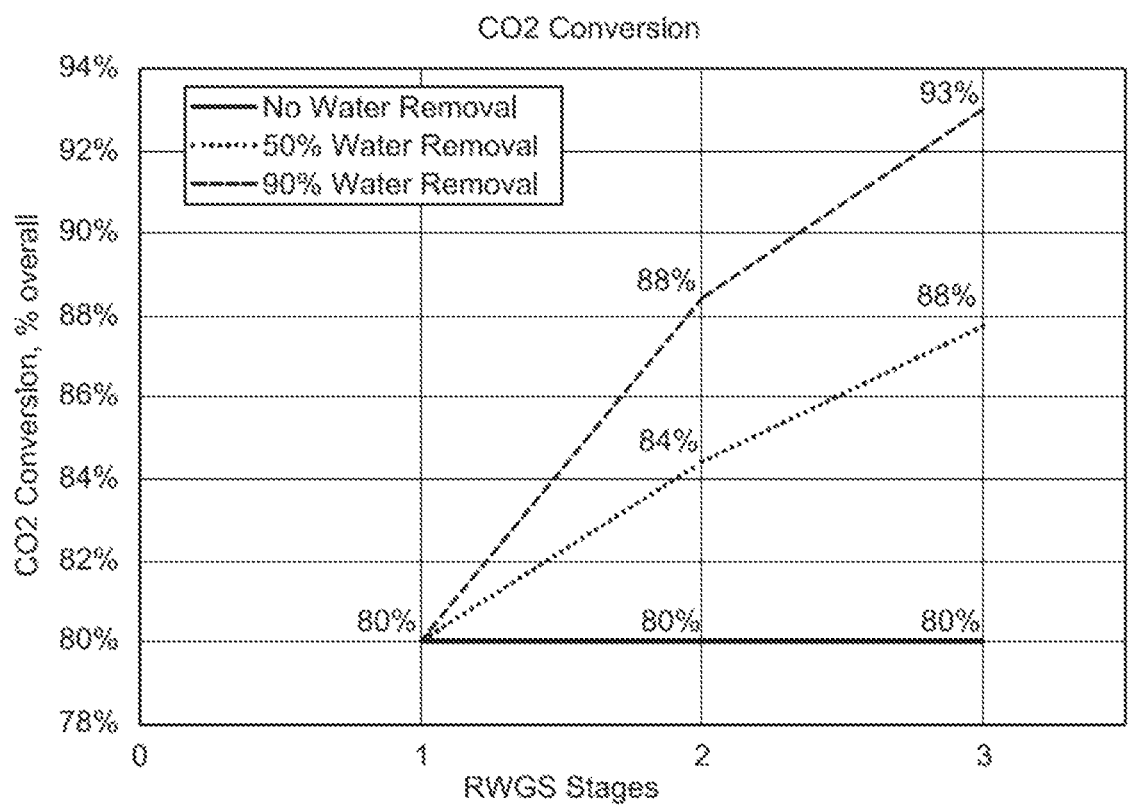
FIG. 10 is a graphical plot $CO_2$ Conversion as function of water removal (different curves) and number of RWGS reactor stages for the Examples.
Figure 11:
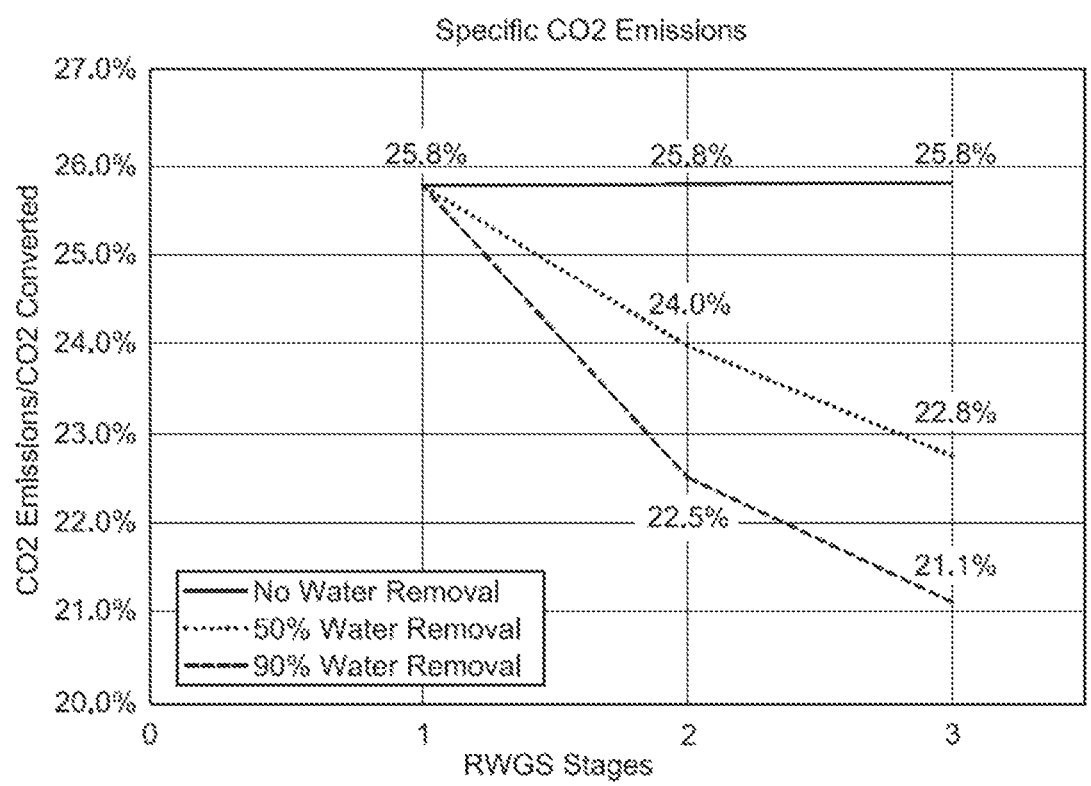
FIG. 11 is a graphical plot $CO_2$ Natural Gas Firing Emissions/$CO_2$ Converted as function of water removal (different curves) and number of RWGS reactor stages for the Examples.

A summary of the Example simulations is presented in Table 10. Plots of $CO_2$ Conversion (FIG. 10) and $CO_2$ Natural Gas Firing Emissions/$CO_2$ Converted (FIG. 11) as function of water removal (different curves) and number of RWGS reactor stages are shown in FIGS. 10 and 11. The Examples clearly demonstrate the benefits of multi-stage RWGS reactor with inter-stage water removal, particularly when the water removal is performed in situ and with heat integration.

$CO_2$ emissions can be further reduced and/or avoided by other means of heating (e.g. electric, $H_2$-fired, waste heat integration, etc.) and/or by $CO_2$ capture from flue gas.

Various modifications and alterations that do not depart from the scope and spirit of this invention will become apparent to those skilled in the art. This invention is not to be duly limited to the illustrative embodiments set forth herein.

What is claimed is:

1. A process for the production of syngas, the process comprising:
   (i) reacting at least a portion of carbon dioxide with hydrogen within an initial reactor to produce an initial product stream including carbon monoxide, water, unreacted carbon dioxide, and unreacted hydrogen; and
   (ii) reacting at least a portion of the unreacted carbon dioxide and unreacted hydrogen within a reactor downstream of the initial reactor to thereby produce a product stream including carbon monoxide, water, unreacted carbon dioxide, and unreacted hydrogen, where the initial product stream has a temperature T1 when exiting the initial reactor, where the product stream has a temperature T2 when exiting the downstream reactor, and where T2>T1, and where T1 is from about 300 to about 1000° C., and where T2 is from about 500 to about 1200° C.,
   wherein the initial reactor is an adiabatic reactor and the reactor downstream of the initial reactor is a fired-tubular reactor.

2. The process of claim 1, where the initial reactor includes reactants, and where the carbon dioxide and the hydrogen include at least 50 mol % of the reactants within the initial reactor.

TABLE 10

| Stream | | CO2 Feed | H2 Feed | Mixed Feed | RWGS 1 Feed | RWGS 1 Effluent | Water 1 | R1 to R2 Syngas | RWGS 2 Feed | RWGS 2 Effluent |
|---|---|---|---|---|---|---|---|---|---|---|
| Stream No. | | 6001 | 6002 | 6003 | 6004 | 6005 | 6006 | 6007 | 6008 | 6009 |
| Temperature | F. | 100 | 100 | 83 | 1254 | 1000 | 1000 | 1000 | 1105 | 1000 |
| Pressure | psia | 565 | 565 | 550 | 530 | 510 | 510 | 505 | 485 | 465 |
| Total Flow | lbmol/hr | 1500.0 | 4955.0 | 6758.8 | 6758.8 | 6758.8 | 845.1 | 5913.6 | 5913.6 | 5913.6 |
| CO | lbmol/hr | 0.0 | 0.0 | 0.0 | 0.0 | 939.0 | 0.0 | 939.0 | 939.0 | 1254.5 |
| H2 | lbmol/hr | 0.0 | 4955.0 | 4955.0 | 4955.0 | 4016.0 | 0.0 | 4016.0 | 4016.0 | 3700.5 |
| CO2 | lbmol/hr | 1500.0 | 0.0 | 1803.8 | 1803.8 | 864.7 | 0.0 | 864.7 | 864.7 | 549.2 |
| H2O | lbmol/hr | 0.0 | 0.0 | 0.0 | 0.0 | 939.0 | 845.1 | 93.9 | 93.9 | 409.4 |

| Stream | | Water 2 | RWGS 3 Feed | RWGS 3 Effluent | Cooled Syngas | Product Syngas 3 | Water 3 | Captured CO2 | Total CO2 Feed |
|---|---|---|---|---|---|---|---|---|---|
| Stream No. | | 6010 | 6011 | 6012 | 6013 | 6014 | 6015 | 6016 | 6017 |
| Temperature | F. | 1000 | 1000 | 1742 | 100 | 100 | 100 | 100 | 100 |
| Pressure | psia | 465 | 460 | 440 | 415 | 415 | 415 | 565 | 565 |
| Total Flow | lbmol/hr | 368.5 | 5545.2 | 5545.2 | 5545.2 | 5118.0 | 427.1 | 303.8 | 1803.8 |
| CO | lbmol/hr | 0.0 | 1254.5 | 1651.8 | 1651.8 | 1651.8 | 0.0 | 0.0 | 0.0 |
| H2 | lbmol/hr | 0.0 | 3700.5 | 3303.2 | 3303.2 | 3303.2 | 0.0 | 0.0 | 0.0 |
| CO2 | lbmol/hr | 0.0 | 549.2 | 151.9 | 151.9 | 151.9 | 0.0 | 303.8 | 1803.8 |
| H2O | lbmol/hr | 368.5 | 40.9 | 438.2 | 438.2 | 11.1 | 427.1 | 0.0 | 0.0 |

3. The process of claim 2, where the initial reactor includes less than 10 mol % methane relative to the total moles of reactants within the initial reactor.

4. The process of claim 1, where the reactor downstream of the initial reactor is a final reactor in series, where the product stream produced by said final reactor is the final product stream, and where the process further includes reacting unreacted carbon dioxide and unreacted hydrogen within said initial product stream within one or more reactors positioned between the initial reactor and the final reactor.

5. The process of claim 4, where the one or more reactors positioned between the initial reactor and the final reactor produce a final intermediary product stream, which includes carbon monoxide, water, unreacted hydrogen, and unreacted carbon dioxide, and where said unreacted hydrogen and unreacted carbon dioxide within said final intermediary product stream are reacted within the final reactor.

6. The process of claim 4, further comprising (i) removing at least a portion of the water from the initial product stream prior to said step of reacting at least a portion of the unreacted carbon dioxide and unreacted hydrogen within the final reactor or (ii) removing at least a portion of the water from the intermediate product stream prior to said step of reacting unreacted carbon dioxide and unreacted hydrogen within one or more reactors positioned between the initial reactor and the final reactor.

7. The process of claim 1, where said step of reacting at least a portion of carbon dioxide with hydrogen within an initial reactor takes place adiabatically.

8. The process of claim 4, further including the step of introducing heat to the final reactor, where said step of introducing heat to the final reactor generates carbon dioxide and produces an exhaust stream containing $CO_2$, and further including capturing at least a portion of the $CO_2$ contained in said exhaust stream to form a captured stream containing $CO_2$, and further including introducing at least a portion of the $CO_2$ contained in said captured stream to the final reactor or to a step upstream of the final reactor for conversion to carbon monoxide.

9. The process of claim 1, further comprising (i) providing a stream including carbon dioxide, (ii) providing a stream including hydrogen, (iii) combining the stream including carbon dioxide with the stream including hydrogen to form a reactant mixture, (iv) optionally heating the reactant mixture to form a heated reactant mixture, and (v) introducing at least one of the reactant mixture and the heated reactant mixture to the initial reactor.

10. The process of claim 9, where the stream including hydrogen includes greater than 90 mol % hydrogen, and where the stream including carbon dioxide includes greater than 90 mol % carbon dioxide.

11. The process of claim 8, where said step of capturing at least a portion of the exhaust $CO_2$ stream includes capturing at least 50% of the carbon dioxide generated to produce the heat.

12. The process of claim 4, where the final product stream includes carbon monoxide and hydrogen, and where the final product stream is a synthesis gas stream.

13. The process of claim 4, further comprising the step of converting at least a portion of the final product stream to at least one of a hydrocarbon, methanol, and an alcohol.

14. The process of claim 1, where said step of reacting at least a portion of carbon dioxide with hydrogen produces an exhaust stream containing excess heat, and further comprising the step of transferring said excess heat to at least one of the carbon dioxide containing feed stream and the reactant mixture prior to said step of (i) reacting at least a portion of the carbon dioxide with hydrogen in an initial reactor.

15. The process of claim 8, where said step of introducing heat to the final reactor includes introducing heat from a carbon-free heat source, and where the carbon-free heat source includes at least one of electrical power, nuclear power, wind power, solar power, hydropower, combustion of hydrogen, and combustion of a carbon-free fuel.

16. The process of claim 1, further comprising the step of capturing carbon dioxide from a point source to form a captured stream including carbon dioxide stream, and further comprising introducing at least a portion of the captured stream including carbon dioxide to the initial reactor.

17. The process of claim 1, further comprising the step of capturing carbon dioxide from atmospheric air to form a direct-air captured stream including carbon dioxide, and further comprising introducing at least a portion of the direct-air captured stream including carbon dioxide to the initial reactor.

18. A process for the production of syngas, the process comprising:
(i) providing a reactant stream including carbon dioxide;
(ii) providing a reactant stream including hydrogen;
(iii) combining the reactant stream including carbon dioxide with the reactant stream including hydrogen to form a mixed reactant stream;
(iv) heating the mixed reactant stream to form a heated mixed reactant stream;
(v) introducing the heated mixed reactant stream to an adiabatic reactor including a reverse water-gas shift catalyst;
(vi) allowing the hydrogen and carbon dioxide to react within the adiabatic reactor to thereby form an initial product stream including carbon monoxide, water, hydrogen, and carbon dioxide;
(vii) removing the initial product stream from the adiabatic reactor, where said initial product stream, upon exiting the adiabatic reactor, has a temperature T1;
(viii) removing at least a portion of the water in the initial product stream from the initial product stream to form a water-lean initial product stream;
(ix) introducing the initial product stream to a fired-tubular reactor including a reverse water-gas shift catalyst, where said fired-tubular reactor produces an exhaust stream including produced carbon dioxide and excess heat;
(x) heating the product stream to a temperature T3 within the fired-tubular reactor, where T3 is greater than or equal to T1, to thereby react the carbon dioxide and hydrogen within the initial product stream to form a final product stream;
(xi) routing at least a portion of the excess heat to said step of heating the mixed reactant stream to form a heated mixed reactant stream; and
(xii) routing at least a portion of the produced carbon dioxide to said adiabatic reactor, or said fired-tubular reactor.

19. A process for the production of syngas, the process comprising:
(i) providing a reactant stream including carbon dioxide;
(ii) providing a reactant stream including hydrogen;
(iii) combining the reactant stream including carbon dioxide with the reactant stream including hydrogen to form a mixed reactant stream;
(iv) heating the mixed reactant stream to form a heated mixed reactant stream;

(v) introducing the heated mixed reactant stream to an initial adiabatic reactor including a reverse water-gas shift catalyst;
(vi) allowing the hydrogen and carbon dioxide to react within the initial adiabatic reactor to thereby form an initial product stream including carbon monoxide, water, hydrogen, and carbon dioxide;
(vii) removing the initial product stream from the initial adiabatic reactor, where said initial product stream, upon exiting the initial adiabatic reactor, has a temperature T1;
(viii) removing at least a portion of the water in the initial product stream from the initial product stream to form a water-lean initial product stream;
(ix) heating the water-lean initial product stream to form a heated water-lean initial product stream;
(x) introducing the heated water-lean initial product stream to a downstream adiabatic reactor including a reverse water-gas shift catalyst;
(xi) allowing the hydrogen and carbon dioxide to react within the downstream adiabatic reactor to thereby form an intermediary product stream including carbon monoxide, water, hydrogen, and carbon dioxide;
(xii) removing the intermediary product stream from the downstream adiabatic reactor, where said intermediary product stream, upon exiting the downstream adiabatic reactor, has a temperature T2;
(xiii) removing at least a portion of the water in the intermediary product stream to form a water-lean intermediary product stream;
(xiv) optionally heating the water-lean intermediary product stream to form a heated, water-lean intermediary product stream at temperature T02;
(xv) optionally introducing the heated, water-lean intermediary product stream to a downstream adiabatic reactor including a reverse water-gas shift catalyst and allowing the carbon dioxide and hydrogen in the heated, water-lean intermediary product stream to react and thereby ultimately form a final intermediary product stream;
(xvi) introducing the intermediary product stream or the final intermediary product stream to a fired-tubular reactor including a reverse water-gas shift catalyst, where said fired-tubular reactor produces an exhaust stream including produced carbon dioxide and excess heat;
(xvii) heating the intermediary or final intermediary product stream to a temperature T3 within the fired-tubular reactor, where T3 is greater than or equal to T2, and where T3 is greater than or equal to T1, to thereby react the carbon dioxide and hydrogen within the intermediary product stream or the final intermediary product stream to form a final product stream;
(xviii) routing at least a portion of the excess heat to said step of heating the mixed reactant stream to form a heated mixed reactant stream or to said step of heating the initial product stream to form a heated initial product stream; and
(xix) routing at least a portion of the produced carbon dioxide to said adiabatic reactor, said downstream adiabatic reactor, or said fired-tubular reactor.

20. The process of claim 1, where T2 is greater than 800° C.

21. The process of claim 18, where T3 is greater than 800° C.

22. The process of claim 19, where T3 is greater than 800° C.

* * * * *